United States Patent [19]
Relenyi et al.

[11] Patent Number: 5,106,407
[45] Date of Patent: Apr. 21, 1992

[54] IODONES AND METHODS FOR ANTIMICROBIAL USE

[75] Inventors: Attila G. Relenyi, Midland, Mich.; Gerald F. Koser, Munroe Falls, Ohio; Richard W. Walter, Jr., Midland, Mich.; William J. Kruper, Jr., Sanford, Mich.; Ravi B. Shankar, Midland, Mich.; Anthony P. Zelinko, Sanford, Mich.

[73] Assignee: The Dow Chemical Company, Midland, Mich.

[21] Appl. No.: 445,901

[22] Filed: Dec. 4, 1989

Related U.S. Application Data

[63] Continuation-in-part of Ser. No. 201,644, Jun. 1, 1988, abandoned, which is a continuation-in-part of Ser. No. 927,284, Nov. 4, 1986, abandoned, which is a continuation-in-part of Ser. No. 794,950, Nov. 4, 1985, abandoned, and a continuation-in-part of Ser. No. 856,923, Apr. 28, 1986, abandoned, which is a continuation of Ser. No. 607,022, May 4, 1984, abandoned.

[51] Int. Cl.$^5$ .................. A01N 43/16; A61K 31/335; C07D 309/06
[52] U.S. Cl. .................. 71/88; 549/294; 549/285; 549/274; 549/313; 71/94; 71/95; 71/103; 71/108; 71/114; 71/118; 544/314; 514/456; 514/457; 514/463; 514/464; 514/465; 514/401; 514/676; 514/677; 514/678; 514/681; 514/682; 514/683; 514/68; 514/568; 514/569; 514/452; 514/330; 514/309; 514/26; 514/274; 514/312; 568/306; 568/20; 568/31; 564/170; 564/183; 564/185; 564/90; 564/92; 564/93; 560/46; 560/51; 560/53; 562/549; 562/461; 562/462; 562/463; 546/155; 546/141; 546/219
[58] Field of Search .............. 568/306, 20, 31; 514/676, 677, 678, 681, 682, 683, 684, 568, 569, 452, 456, 457, 463, 464, 465, 461, 617, 622, 604, 330, 309, 269, 274, 312, 456; 549/274, 285, 294, 313; 560/51, 53, 46; 562/549, 461, 462, 463; 564/170, 183, 185, 90, 92, 93; 546/155, 141, 219; 544/311, 314; 71/88, 114, 118, 108, 94, 95, 103, 98

[56] References Cited

U.S. PATENT DOCUMENTS

| | | | |
|---|---|---|---|
| 3,622,586 | 11/1971 | Jezic | 546/296 |
| 3,712,920 | 1/1973 | Jezic | 549/81 |
| 3,734,928 | 5/1973 | Jezic | 568/631 |
| 3,759,989 | 9/1973 | Jezic | 568/631 |
| 3,765,864 | 10/1973 | Kerst et al. | 544/301 |
| 3,896,140 | 7/1975 | Plepys et al. | 548/247 |
| 3,952,028 | 4/1976 | Jezic | 570/182 |
| 4,193,935 | 3/1980 | Cannon | 260/505 |
| 4,310,469 | 1/1982 | Crivello | 260/446 |
| 4,348,525 | 9/1982 | Koser et al. | 546/346 |
| 4,394,322 | 7/1983 | Beach et al. | 260/440 |
| 4,399,071 | 8/1983 | Crivello et al. | 568/6 |
| 4,450,360 | 5/1984 | Crivello et al. | 568/8 |

FOREIGN PATENT DOCUMENTS 0145653 6/1985 European Pat. Off. .
0160322 11/1985 European Pat. Off. .

OTHER PUBLICATIONS

Pongratz, et al., *Monatshefte fur Chemie*, "Ylide von Heterocyclen, VIII," 115, pp. 231–242 (1984).
Kapp et al. (II), *Naturforsch.*, B., 38, pp. 398–403 (1983).
Das Gupta, *Indian J. Chem. B.*, "A facile one-step synthesis of 4-hydroxycoumarin," p. 511 (1981).
Relenyi, Dissertation, University of Akron, May 1982.
Patai et al, The Chemistry of Func. Groups, Suppl. D., (1983), pp. 771–811, John Wiley & Sons.

(List continued on next page.)

*Primary Examiner*—Richard L. Raymond
*Assistant Examiner*—Mark A. Russell

[57] ABSTRACT

The present invention discloses the antimicrobial utility of certain iodonium ylide compounds. The particular iodonium ylide compounds are phenyl iodonium ylides having an ortho substituent that stabilizes the positive charge on the polyvalent iodine by a nonbonded electrostatic interaction. The polyvalent iodine is further stabilized by a cyclic 1,3-dicarbonyl anion.

9 Claims, 2 Drawing Sheets

OTHER PUBLICATIONS

Neiland et al, vol. 141, No. 4, pp. 872–874, Dec. 1961, A New Principle to be Applied in The Preparation of Iodonium Compounds.

Neiland, O., vol. 1, No. 10, pp. 1858–1862, Oct. 1965, Iodonium Derivatives of β-Diketones.

Karele et al, No. 2, pp. 245–248, Feb. 1973, Iodonium Derivatives of Heterocyclic Compounds.

Varvoglis, A., pp. 709–723, Polyvalent Iodine Compounds in Organic Synthesis.

Neiland et al, vol. 1, No. 10, pp. 1854–1857, Oct. 1965, Iodonium Derivatives of β-Diketones.

Neiland et al, vol. 31, No. 1, pp. 146–156, Jan. 1961, Iodonium Derivatives of β-Diketones.

Neiland et al, vol. 2, No. 3, pp. 488–492, Mar. 1968, Iodonium Derivatives of β-Diketones.

Zincke et al, Ber 48, pp. 1242–1254, Uber 1,2-Amino--phenyl—mercaptan.

Organic Syntheses Collective vol. 3, pp. 482–485, Iodobenzene Dichloride.

Sartori et al, Chem. Ber. 100, pp. 1633–1637 (1967), Perfluoracycloxy-Verbindungen des positiven Jods.

Kappe et al, (I), Iodonium- und Pyridinium-Ylide, Von Malonylheterocyclen, Chem. Ber III, pp. 3857–3866 (1978).

Habib et al, Ylides of Heterocycles, Heterocycl. Chem. (1984), 21(2), pp. 385–388 Eng.

Karele et al, vol. 4, No. 4, pp. 643–648, Apr. 1968, Iodonium Derivatives of β-Dicarbonyl Compounds.

Neiland et al, vol. 7, No. 8, pp. 1611–1615, Aug. 1971, Iodonium Derivatives of β-Diketones.

Neiland et al, vol. 6, No. 12, pp. 2509–2512, Dec. 1970, Iodonium Derivatives of β-Diketones.

Karele et al, vol. 4, No. 10, pp. 1818–1822, Oct. 1968, Iodonium Derivatives of β-Dicarbonyl Compounds.

Koser, Gerald F., "Hypervalent Halogen Compounds", *The Chemistry of Functional Groups, Supplemental D*, Edited by S. Patai and Z. Rappoport, Chap. 18, pp. 721–811 (1983).

Koser, Gerald F., "Halonium Ions", *The Chemistry of Functional Groups, Supplemental D*, Edited by S. Patai and Z. Rappoport, Chap. 25, pp. 1265–1351 (1983).

IODONES AND METHODS FOR ANTIMICROBIAL USE

CROSS-REFERENCE TO RELATED APPLICATIONS

This application is a continuation-in-part of application Ser. No. 07/201,644, filed Jun. 1, 1988, now abandoned, which is a continuation-in-part of application Ser. No. 927,284, filed Nov. 4, 1986, now abandoned, which is a continuation-in-part of application Ser. No. 794,950, filed Nov. 4, 1985, now abandoned and application Ser. No. 856,923, filed Apr. 28, 1986, now abandoned which is a continuation of application Ser. No. 607,022, filed May 4, 1984, now abandoned.

BACKGROUND OF THE INVENTION

The desirability of identifying or discovering new antimicrobial agents is widely recognized. New antimicrobial agents are desired for several reasons; these include, but are not limited to, development of microbe strains resistant to known antimicrobials, undesirable interactions of certain known antimicrobials with the medium or product in which the antimicrobial is used, and high toxicity of certain known antimicrobials to certain non-target organisms such as mammals.

Certain polyvalent iodine compounds are known to be effective antimicrobial agents. These known antimicrobial compounds are salts (see, for example, U.S. Pat. Nos. 4,440,943 and 4,513,137).

Iodones are iodonium ylide compounds that are a class of compounds of which little is known. It has now been discovered that certain iodones are iodonium ylides are effective antimicrobial agents.

In his book entitled *Ylid Chemistry* (A. William Johnson, *Ylid Chemistry*, Academic Press, New York and London, 1966, pp. 1–4), A. W. Johnson defines an ylid (typically spelled 'ylide' in the current literature) "as a substance in which a carbanion is attached directly to a heteroatom carrying a high degree of positive charge". He further states that "this definition is intended to include those resonance hybrid molecules in which there is an important contributing structure which meets the original definition". There is a clear distinction between onium salts and onium ylides. In an onium salt, the positive charge on the heteroatom (i.e., a non-carbon atom) is balanced by the negative charge of a counteranion electrostatically associated with the onium ion (i.e., organic cation). In an onium ylide, the positive charge on the heteroatom is balanced by the negative charge of a localized or delocalized carbanion covalently bound to the onium center. Some examples are given below:

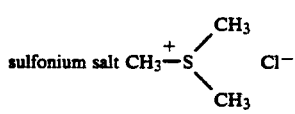

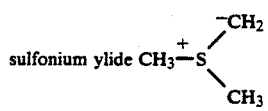

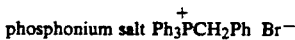

-continued

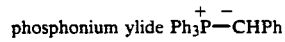

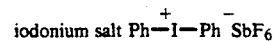

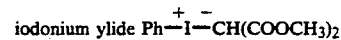

Notice that the protonation of an ylide with a strong acid would give an onium salt. Conversely, the treatment of an onium salt with a strong base would give an ylide; e.g.,

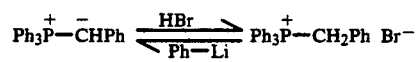

Ylides may sometimes be referred to as "internal or inner salts", "betaines" or "zwitterions". For example, iodonium ylides derived from phenols have been described as:

ylides: P. B. Kokil and P. M. Nair, Tetrahedron Lett. 4113–4116 (1977)

zwitterions: S. Spyroudis and A. Varvoglis, *J. Chem. Soc. Perkin Trans.* I 135–137 (1984).

inner salt: S. W. Page et al., *J. Am. Chem. Soc.*, 101, 5858–5860 (1979). They qualify as ylides because of resonance structure II below:

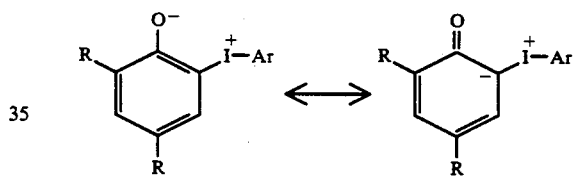

Iodonium ylides derived from β-dicarbonyl compounds are typically called betaines. For example, see B. Y. Karele and O. Y. Neiland, *J. Org. Chem. USSR (Engl.)*, 2, 1656–1658 (1966).

Such terms are synonymous and more general than the term "ylide" and include all organic molecules in which a positive charge center is internally compensated by a negative charge center. However, while it is true that all ylides are internal salts, betaines and zwitterions, it is not true that all internal salts, betaines and zwitterions are ylides. Examples of internal salts (betaines, zwitterions) that are not ylides are shown below. They are not ylides because the negative charge center is neither carbanionic nor directly bound to the onium center.

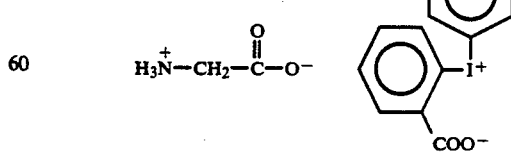

Sometimes ylides are represented in such a way that they appear, at first glance, to be betaines but not ylides. A case in point is the representation of "phenyldimedonyliodone" as an enolate betaine.

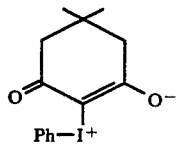

However, phenyldimedonyliodone may be properly regarded as an iodonium ylide since a complete electronic description of the molecule must include the resonance structure below in which a carbanion is directly bound to the iodonium center.

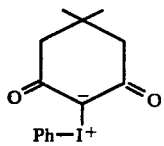

SUMMARY OF THE INVENTION

The present invention is directed to a method of inhibiting the growth of microorganisms such as bacteria, algae and fungi and to antimicrobial compositions containing certain iodonium ylide compounds as antimicrobial agents. Certain of the iodonium ylide compounds described herein are novel and thus the present invention is also directed to those novel compounds. The compounds employed in the methods and compositions of this invention advantageously have the formula

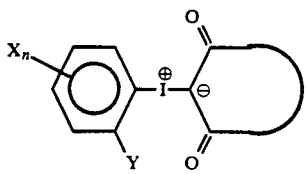

wherein each
X independently represents halo, alkyl of 1 to 4 carbon atoms inclusive, or alkoxy of 1 to 4 carbon atoms inclusive;
n represents an integer from 0 to 2;
Y represents a functional group capable of stabilizing the positive charge on the polyvalent iodine by a proximal nonbonded electrostatic interaction:

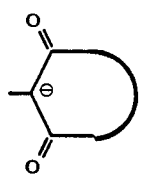

represents a cyclic 1,3-dione anion:
and their hydrates and alcoholates.

With respect to Y, the phrase "a functional group capable of stabilizing the positive charge on the polyvalent iodine by a proximal nonbonded electrostatic interaction" refers to a functional group which contains an electronegative atom, preferably an oxygen atom, which is capable of bearing a negative or partial negative charge. This electronegative atom is conformationally or configurationally constrained in the vicinity of the hypervalent iodine atom of the ylide so that the hypervalent iodine may be electronically stabilized by a nonbonded interaction. Such functional groups include, but are not limited to, nitro, alkyl sulfinyl, alkyl sulfonyl, carboxylic acid and the esters and amides thereof and sulfonic acid and the amides thereof. The preferred groups are nitro, alkyl sulfinyl and alkyl sulfonyl.

With respect to

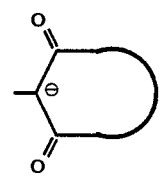

by a "cyclic 1,3-dione anion" is meant an anionic 1,3-dicarbonyl compound in which the conformational freedom of the carbonyls is restricted by incorporation into a ring system. The negative charge is nominally located at the acidic 2-position, but is dispersed through the carbonyl groups flanking the 2-position, the same position to which the iodine is covalently bound. The important feature is the restricted rotation of the 1,3-dicarbonyl network by incorporation into a ring system. It follows, therefore, that the exact nature of the ring system is not of critical importance. The 1,3-dione may be incorporated into monocyclic or polycyclic, saturated or unsaturated ring systems. The ring systems may optionally contain heteroatoms such as, for example, oxygen and nitrogen. Polycyclic ring systems may contain an aromatic portion. The ring systems may be optionally substituted with from 1 to 2 substituents selected from the group consisting of halo, alkyl of 1 to 4 carbon atoms inclusive, alkoxy of 1 to 4 carbon atoms inclusive and carboxyl. Such cyclic 1,3-dione anions include, but are not limited to, the following skeletal types:

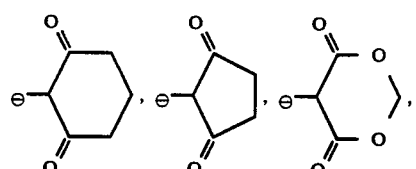

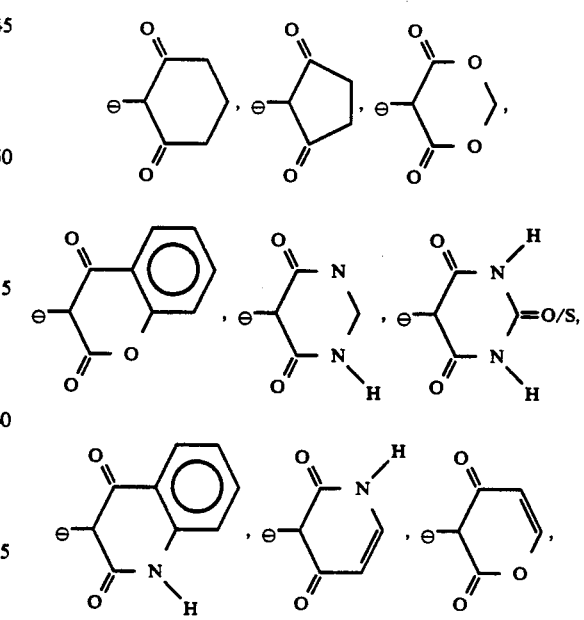

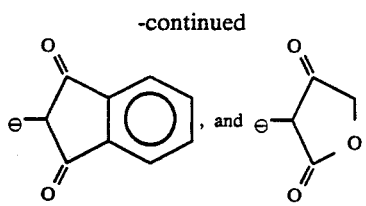
-continued

These skeletal types may be optionally substituted as described above. Preferred compounds are those containing only carbon or carbon and oxygen in the skeletal framework of the cyclic dicarbonyl anion.

As used herein, the term halo refers to fluoro, chloro, bromo or iodo; the term alkyl refers to a straight-chained or branched hydrocarbon radical of from 1 to 4 carbon atoms inclusive; the term alkoxy refers to a straight-chained or branched alkoxy radical of 1 to 4 carbon atoms inclusive.

With the exception of (2-nitrophenyl)-iodonium 4,4-dimethyl-2,6-dioxocyclohexylide (Example 14) and (2-nitrophenyl)-iodonium 2,2-dimethyl-4,6-dioxo-1,3-dioxan-5-ylide (Example 19) the compounds of formula (I) are new.

As appreciated in the art, not all of the compounds disclosed herein are active at the same concentrations or against the same microbial species. That is, there is some compound-to-compound variation in antimicrobial potency and spectrum of antimicrobial activity.

The present invention is also directed to a method for inhibiting microorganisms, particularly bacteria, fungi, and algae which comprises contacting said microorganisms or habitat thereof with an effective amount of the compound of Formula I.

As used herein, the term "effective amount" refers to that amount of one or a mixture of two or more of the compounds of Formula I needed to exhibit inhibition of selected organisms. Typically, this amount varies from about 100 parts per billion (ppb) to about 5000 parts per million (ppm) by weight depending upon the particular compound tested and organism treated.

The terms "inhibition", "inhibit" or "inhibiting" refer to suppression, control, stasis, kill or any other interference with the normal life processes of microorganisms that is adverse to such microorganisms.

In the compounds employed in the methods and compositions of the present invention, it is to be noted that all substituent groups are sterically compatible with each other. The term "sterically compatible" is employed to designate substituent groups which are not affected by steric hindrance as this term is defined in "The Condensed Chemical Dictionary", 7th edition, Reinhold Publishing Co., N.Y., page 893 (1966) which definition is as follows:

"steric hindrance. A characteristic of molecular structure in which the molecules have a spatial arrangement of their atoms such that a given reaction with another molecule is prevented or retarded in rate."

Sterically compatible may be further defined as reacting compounds having substituents whose physical bulk does not require confinement within volumes insufficient for the exercise of their normal behavior as discussed in "Organic Chemistry" of D. J. Cram and G. Hammond, 2nd edition, McGraw-Hill Book Company, N.Y., page 215 (1964).

DETAILED DESCRIPTION OF THE INVENTION

Figure 1:
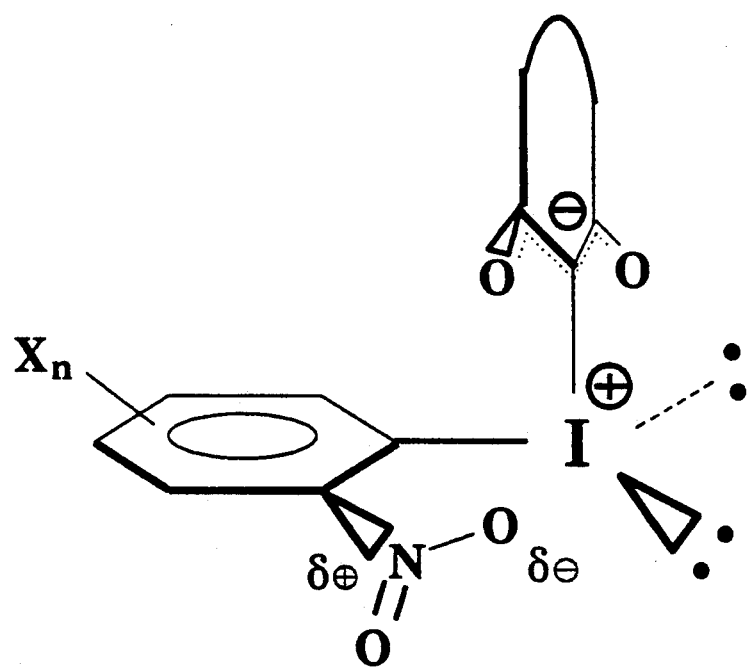
FIGS. 1 and 2 depict two different representations of the spatial arrangement of an ortho nitro group and of a cyclic 1,3-dicarbonyl group that stabilizes the positive charge of the iodine atom of the iodonium ylid. The negatively polarized oxygen atoms, by virtue of their proximity to the positively charged iodine, stabilize the charge by a coulombic interaction.
Figure 2:
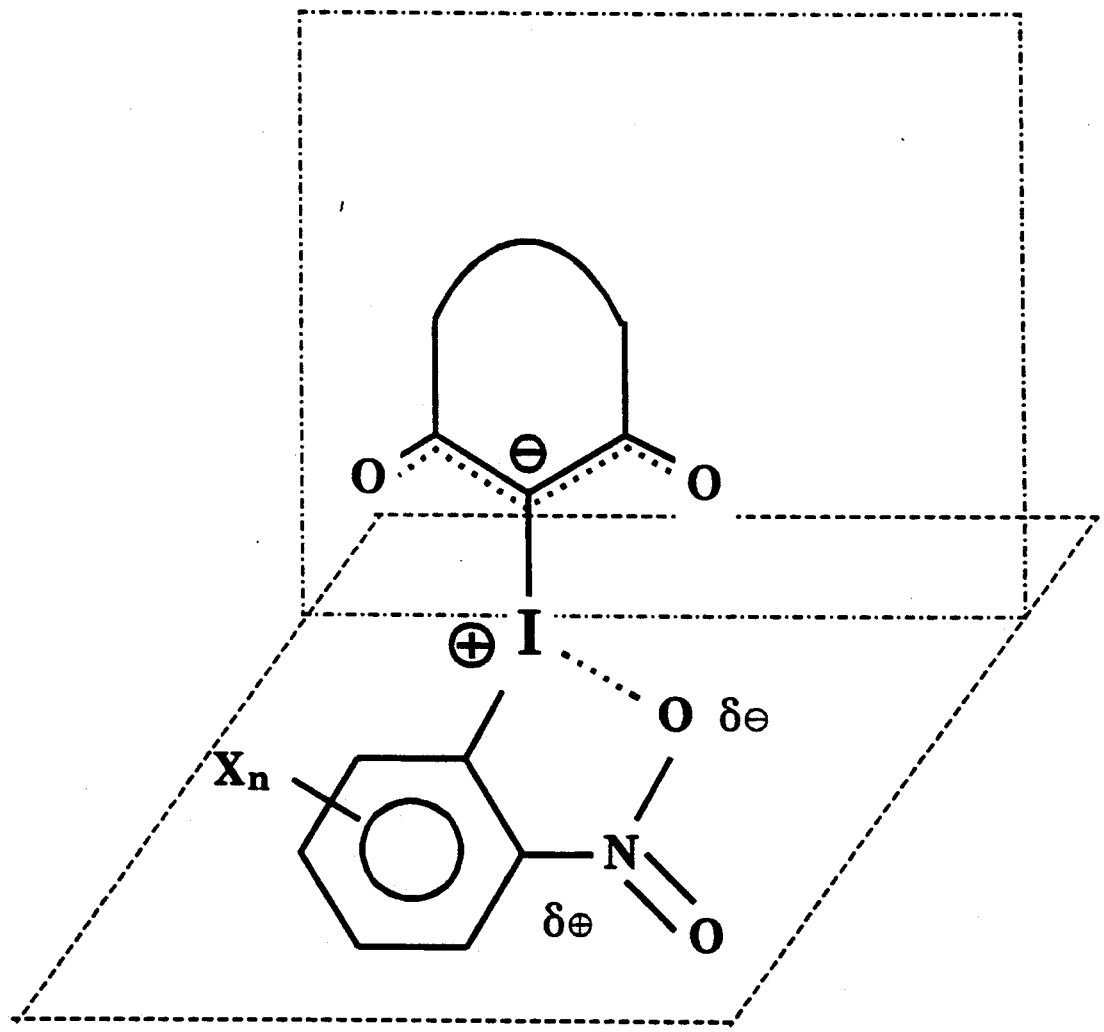

The compounds employed in the methods and compositions of the present invention are prepared by using procedures known to the art. The methods and certain starting materials used to prepare these compounds are taught, for example, in *Structure Elucidation, Mechanism and Synthetic Applications of Organoiodone (III) Compounds: Dibenziodoles, Dibenziodolium Salts, Phenyl dimedonyliodones, Phenylhydroxytosyloxyiodine and Phenyl methoxytosyloxyiodine* (A. G. Relenyi, 1982, University of Akron Library, Akron, Ohio); O. Neiland and B. Karele, *J. Org. Chem. USSR (Engl. Transl.)*, 7, 1674–1677 (1971); A. K. Das Gupta, R. M. Chatterjee and K. R. Das, *Indian J. Chem. Sect. B*(20B) 511 (1981); A. Varvoglis, *Synthesis* 709 (1984); H. Zincke and G. Siebert, *Ber.*, 48, 1242 (1915); *Organic Synthesis Collective Volume* 3, p. 484; M. Schmeisser, K. Dahmen and P. Sartori, *Chem. Ber.* 100, 1633–1637 (1967); and *The Chemistry of Functional Groups, Supplement D* (Patai and Rappoport, editors), John Wiley and Sons, Ltd., 771–811 (1983); each of which (including references therein) are incorporated herein by reference.

For example, those compounds of Formula I in which

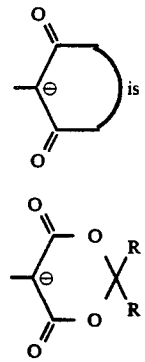

wherein each R is independently hydrogen or alkyl of 1 to 4 carbon atoms may be prepared by the following procedure. Malonic acid is reacted with the necessary R substituted ketone in the presence of a strong acid catalyst such as sulfuric acid or hydrochloric acid to form the desired malonate; this reaction is illustrated by the following reaction sequence;

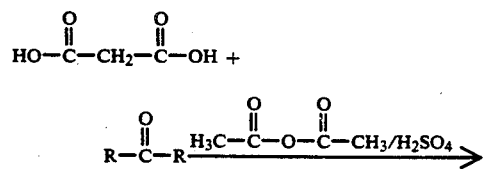

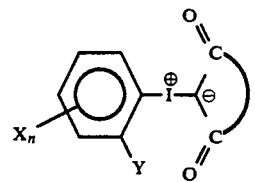

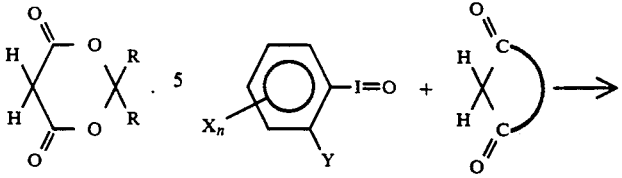

The malonate is then reacted with an $X_n$ and Y-substituted iodosobenzene in an inert organic solvent such as chloroform, dichloromethane or 1,1,2,2-tetrachloroethylene; this reaction is illustrated by the following reaction sequence:

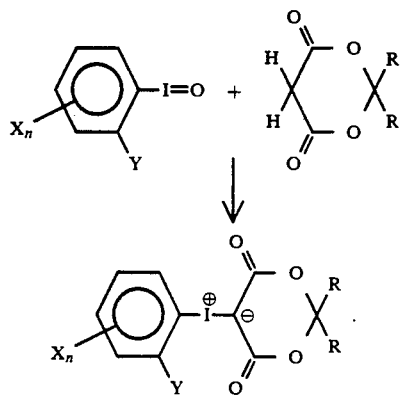

In an alternate procedure, the malonate is reacted with an $X_n$ and Y-substituted iodosobenzene dicarboxylate in a methanolic solution of KOH or NaOH; this reaction is illustrated by the following reaction sequence:

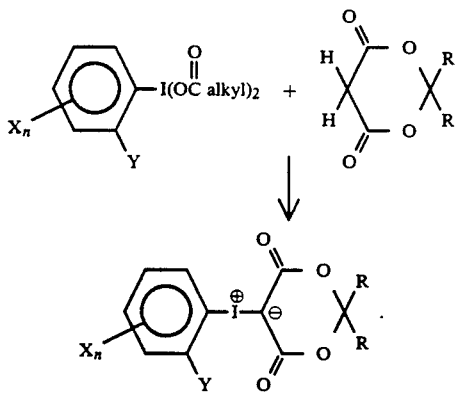

Similarly, the other compounds represented by Formula I may be prepared in an analogous manner as, for example, by the reaction of the appropriate $X_n$ and Y-substituted iodosobenzene or iodosobenzene dicarboxylate with a cyclic 1,3-dicarbonyl compound.

For instance, the appropriate 1,3-dicarbonyl compound can be reacted with $X_n$ and Y-substituted iodosobenzene in an inert organic solvent such as chloroform (or with an $X_n$ and Y-substituted iodosobenzene dicarboxylate in basic methanol): this reaction is illustrated by the following reaction sequence:

Starting materials not specifically disclosed in the art can be prepared by procedures analogous to the prior art procedures using the appropriate starting compounds.

It has heretofore been unknown that the compounds of Formula I, can be used in valuable antimicrobial applications (i.e., as a bactericide, fungicide, algaecide and the like). For example, the compounds of Formula I or compositions containing one or more of them as the active antimicrobial constituent can be incorporated into or upon plaster, ink, cosmetic formulations, wallboard, textiles, paper, adhesives, soaps, synthetic detergents, cutting oils, polymeric materials, embalming fluids, oil-base paints, latex paints and any other aqueous based system in order to prevent the attack of various microbial pests and thus avoid the resultant economic loss due to the degradation of such products by the microorganisms. Also the compounds can be distributed in textiles, cellulosic materials or in grain or can be employed in the impregnation of wood and lumber to preserve and protect such products from the attack of the organisms of rot, mold and decay.

A preferred antimicrobial application for the compounds of Formula I is in the prevention of slime accumulation in water cooling towers. These compounds typically have low minimum inhibitory concentrations against aqueous-borne biofoulants often found in industrial cooling towers such as, for example, *Pseudomonas aeruginosa* and *Enterobacter aerogenes*. Further, the compounds typically exhibit good hydrolytic stability (half-life of days to months) and are thus persistent in aqueous media. Because of the low concentrations needed to inhibit slime buildup in this environment, subsequent degradation products will also be present in low concentrations. The most preferred antimicrobial application for the compounds of Formula I is as a long term preservative, particularly in alkaline media. As used herein the term "preservative" refers to the ability of a desired compound to prevent microbiological deterioration and/or contamination of a medium into which said desired compound has been incorporated. Accordingly, the preservative compounds of Formula I have the ability to inhibit microorganisms even after repeated insults from such microorganisms. Therefore, the most preferred antimicrobial application for the compounds of Formula I includes incorporation of the compounds of Formula I into cosmetics, various latexes such as adhesives, textiles, paints, papers and the like which may be subject to microbiological contamination and/or deterioration. Similarly, another preferred antimicrobial application for the compounds of Formula I is as a preservative in metalworking fluids. Especially preferred for use as preservatives and in the water cooling tower applications described above are the compounds (2-nitrophenyl)-iodonium 2,2-dimethyl-4,6-dioxo-1,3-dioxan-5-ylide and (2-nitrophenyl)iodonium 2,6-dioxocyclohexylide.

In the method of the present invention, the microorganisms (e.g., bacteria, fungi or algae), or habitat thereof are contacted with an antimicrobially active iodonium ylide compound or with a composition containing an antimicrobially active iodonium ylide compound. The microorganisms to be inhibited are contacted with at least an effective amount of the antimicrobially active iodonium ylide compound. The antimicrobial compositions of this invention contain an amount of from about 0.00001 percent to about 99.99 percent by weight of the antimicrobially active iodonium ylide compound: preferably from about 0.0001 percent to about 50 percent; and most preferably from about 0.0001 to about 10 percent.

The antimicrobial compositions of this invention can also contain, in addition to the effective amount of the iodonium ylide compound, one or more additives typically employed in the art. Such additives can be inert or can be antimicrobial composition adjuvants.

Certain of the compounds of the present invention may exist as complexes, e.g., hydrates and alcoholates. Such complexes are included in the scope of the invention.

The following examples further illustrate the present invention and are not to be construed as a limitation thereon. Those compounds without accompanying descriptive preparatory procedures were prepared using appropriate starting materials following procedures analogous to those described herein.

EXAMPLE 1

2-Nitro-4-chloroiodobenzene

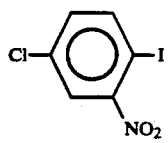

A 1M aqueous solution of sodium nitrite (50 milliliters (mL)) was added dropwise to a cold (3° C.) stirred mixture of 4-chloro-2-nitroaniline (8.63 grams (g), 50 millimoles (mmol)) in 6M HCl (150 mL) over a 45 minute (min) period with subsequent addition of about 5 g of urea during 30 min. An aqueous solution of potassium iodide (60 mL, 1M) was dripped into the resulting orange solution over a period of 35 min at 5° C. After an additional 45 min, the desired product, which had separated from solution, was isolated by filtration and then dried in air; yield, 13.73 g (brown powder): m.p. 50°-60° C.

EXAMPLE 2

2-Nitro-4-methyl(dichloroiodo)benzene

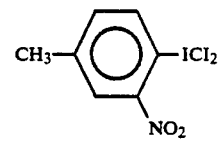

Into a cold (about 5° C.), stirred solution of 2-nitro-4-methyliodobenzene (5.0 g, 19 mmol) in CHCl$_3$ (40 mL) was introduced a stream of chlorine gas via a dry ice-/acetone condensor. Chlorination was continued for 1 hour (hr), during which time the desired compound, a yellow solid, precipitated from solution. Subsequent filtration and air drying gave the desired title compound; yield, 2.9 g; m.p. 50°-52° C.

EXAMPLE 3

2-Nitro-4-chloro(dichloroiodo)benzene

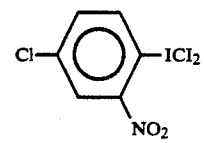

Into a cold (about 2° C.) methylene chloride (50 mL) solution of 2-nitro-4-chloroiodobenzene (6.0 g, 21.2 mmol) a stream of chlorine gas was introduced via a dry ice/acetone-cooled condenser. Chlorination was continued for about 1.5 hr. The reaction mixture was then stored overnight in a refrigerator whereupon the desired product separated from the solvent as a yellow crystalline solid: yield, 2.38 g: m.p. 53°-60° C.

EXAMPLE 4 o-Nitroiodosobenzene Dichloride

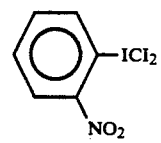

o-Nitroiodobenzene (5.38 g) was mixed with 50 mL of chloroform. To this mixture was added liquified (condensed via a Dry-Ice condenser) chlorine gas while the reaction mixture temperature was maintained at about 25° C. A yellow precipitate formed which was collected by filtration to give 5.66 g of o-nitroiodosobenzene dichloride; m.p. 82°-84° C.

EXAMPLE 5

2-Nitro-4-methyliodosobenzene

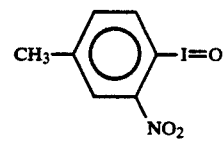

2-Nitro-4-methyl(dichloroiodo)benzene (2.0 g, 6.0 mmol) was added portion-wise, over a period of 15 min, to a cold (5° C.), stirred solution of 20 percent aqueous sodium hydroxide (100 mL). Five min after the addition, the desired product, an orange solid, insoluble in the reaction medium, was isolated by filtration; yield, 1.51g.

EXAMPLE 6

2-Nitro-4-chloroiodosobenzene

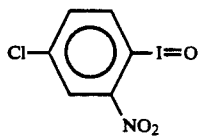

2-Nitro-4-chloro(dichloroiodo)benzene (2.0 g) was added to 100 mL of cold (about 5° C.) 20 percent aqueous solution of sodium hydroxide. The mixture was stirred for 0.5 hr, and the desired orange product was subsequently isolated by filtration and air dried; yield, 1.13 g; m.p. 118° C. (decomposed (dec.)).

EXAMPLE 7

(2-Methylsulfonyl)-iodosobenzene

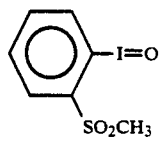

2-Methylsulfonyl iodobenzene (1 g, 3.54 mmol) was suspended in 5 mL of trifluoroacetic anhydride and cooled to about −30° C. To this suspension was added 0.5 mL of concentrated nitric acid and the mixture was allowed to warm at room temperature while stirring for about 4 hr. The solvent was then removed under reduced pressure to give a resultant solid which was dried under high vacuum overnight.

The dried solid was suspended in 25 mL of saturated aqueous sodium bicarbonate and stirred overnight. The resultant bright yellow solid was filtered, air dried and determined to be the desired product. The yield was 780 milligrams (mg) of desired product having a purity of about 90–95 percent, as determined by iodometric titration.

EXAMPLE 8 o-Nitroiodosobenzene

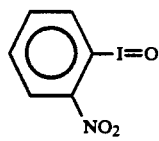

o-Nitroiodosobenzene dichloride (3.0 g) was triturated with 15 mL of 33 percent aqueous potassium hydroxide solution. An additional 20 mL of the aqueous potassium hydroxide solution was added, and the resultant orange powder was collected by filtration, washed with water and then diethyl ether (3×20 mL) to give 1.78 g of o-nitroiodosobenzene as a dark yellow-orange powder.

EXAMPLE 9

Isopropylidene Malonate (Meldrum's Acid)

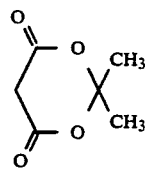

Following the general method of Davidson and Bernhard (J. Amer. Chem. Soc., 70, 3426 (1948)) isopropylidene malonate was prepared as follows: Malonic acid (26.08 g) was mixed with acetic anhydride (31 mL) and then 1.58 g of concentrated sulfuric acid was added whereupon some of the malonic acid dissolved. The resultant mixture was cooled in an ice bath and 21 mL of acetone was added with stirring keeping the temperature below 20° C. The solution was cooled to about 0° C. for about 4 days during which time a yellow color developed and the solution froze. During the 4 day period, the frozen mixture was occasionally thawed, stirred, and allowed to refreeze. After the 4 day period, a solid was recovered from the cold mixture. The solid was washed with 250 mL of ice cold water (about 3–5° C.) and allowed to dry in air to give 21.11 g of white crystalline isopropylidene malonate. The resultant isopropylidene malonate was stored under refrigeration (about 0° C.) to prevent degradation.

EXAMPLE 10

(2-Nitrophenyl)-iodonium 2,5-dioxocyclopentyl-1-ylide

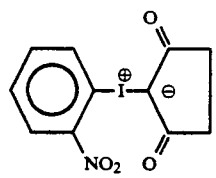

1.73 Grams (0.0176 mol) 1,3-cyclopentanedione and 70 mL acetonitrile were stirred at 22° C. for 2 min to give a milky white suspension. Subsequent addition of solid orange iodosonitrobenzene (4.79 g 0.0181 mol) to the milky white mixture resulted in an immediate color change with a temperature rise of about 2° C. After about 10 min, the reaction mixture was filtered to give a white yellow powder (2.8 g 0.0081 mol) (46.1 percent yield). Approximately 2 g of this powder was dissolved in 200 mL of a 50/50 acetone/methylene chloride mixture and filtered. The resultant yellow filtrate was concentrated at 35° C. to a volume of about which was subsequently 10 mL and filtered to give bright yellow crystals. The yellow crystals were dried in vacuo (0.4 mm Hg, 25° C., 18 hr) to give 1.00 g (0.0029 mol) (23.1 percent yield) (m.p. 135°–140° C.) of the desired product which was identified by PMR, CMR, and elemental composition.

| Analysis (elemental analysis) | | | |
| --- | --- | --- | --- |
|  | C | H | N |
| Calc. for $C_{11}H_8INO_4$: | 38.29 | 2.33 | 4.06 |
| Found: | 38.2 | 2.47 | 3.90 |

EXAMPLE 11

(2-Nitrophenyl)-iodonium 2,6-dioxocyclohexan-1-ylide

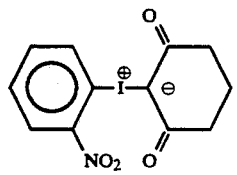

2-Nitroiodosobenzene (1.61 g) and dichloromethane (60 mL) were mixed and stirred at room temperature. To the orange colored mixture was added a solution of 1,3-cyclohexanedione (0.79 g) in 5 mL of dichloromethane. Immediately after the addition, the color changed to yellow and a temperature rise of about 2° C. was observed. The yellow mixture was then stirred for about 2 hr. After such time the dichloromethane was removed from the yellow mixture by evaporation to give a yellow tacky solid which was subsequently dried under a nitrogen stream. The tacky solid was then washed sequentially with water (2×100 mL), hexanes (2×20 mL) and the resultant solid was air dried. The dried solid was further washed with acetone (2×40 mL) and air dried to give 0.740 g of the desired product as a clear medium yellow solid; m.p. 132°-134° C. Product identification was based on CMR, PMR analysis and elemental composition data.

| Analysis (elemental analysis) | | | | |
| --- | --- | --- | --- | --- |
|  | C | H | N | I |
| Calc. for $C_{12}H_{10}INO_4$: | 40.14 | 2.80 | 3.90 | 35.34 |
| Found: | 40.20 | 2.98 | 4.08 | 33.00 |

EXAMPLE 12

((2-Methylsulfonyl)phenyl)-iodonium 4,4-dimethyl-2,6-dioxocyclohexan-1-ylide

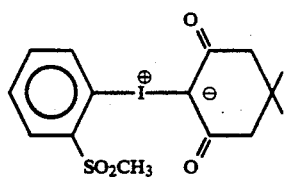

5,5-Dimethyl-1,3-cyclohexanedione, (0.67 mmol, 95 mg) was dissolved in 5 mL of hot methanol and to it was added a solution of o-methylsulfonyliodosobenzene (0.67 mmol, 200 mg) in 10 mL of hot methanol. The resulting solution was concentrated under a nitrogen stream which resulted in crystals. The crystals were dried under vacuum and were determined by PMR and CMR to be the desired product; yield 210 mg; m.p. 178°-180° C.

| Analysis (elemental analysis) | | |
| --- | --- | --- |
|  | C | H |
| Calc. for $C_{15}H_{17}IO_4S$: | 42.86 | 4.08 |
| Found: | 42.90 | 4.15 |

EXAMPLE 13

((2-Methylsulfonyl)phenyl)-iodonium 2,6-dioxocyclohexan-1-ylide

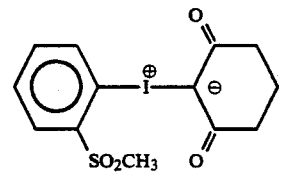

1,3-Cyclohexanedione, (75 mg, 0.67 mmol) was added to a solution consisting of 2-methylsulfonyliodosobenzene (0.67 mmol, 200 mg) and 10 ml of hot methanol. The resultant solution was allowed to cool and was concentrated under a nitrogen stream. The resultant fluffy, white solid was filtered and washed with cold methylene chloride, dried under vacuum and was determined by NMR to be the desired product; yield, 140 mg. Additional product was obtained by concentration of the filtrate to give a solid with m.p. 142°-143° C. (dec).

| Analysis (elemental analysis) | | |
| --- | --- | --- |
|  | C | H |
| Calc. for $C_{13}H_{13}IO_4S$: | 39.81 | 3.34 |
| Found: | 39.90 | 3.48 |

EXAMPLE 14

(2-Nitrophenyl)-iodonium 4,4-dimethyl-2,6-dioxocyclohexylide

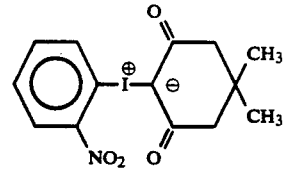

o-Iodosonitrobenzene (1.49 g) and dichloromethane (50 mL) were mixed at room temperature and to the resultant orange colored mixture was added dimedone (0.85 g). Within several min after the addition of dimedone, the color of the mixture gradually changed to a rich yellow with a concurrent rise in temperature of about 2° C. The rich yellow mixture was then stirred for about 2 hr, evaporated, and dried under a nitrogen stream to give a yellow tacky solid. The tacky solid was then washed sequentially with 10 percent aqueous potassium hydroxide (150 mL), distilled water (3×100 mL), and methyl-tert-butyl ether (30 mL) and air dried to give the desired compound; yield, 1.13 g; m.p. 132°-134° C.

EXAMPLE 15

(2-Nitrophenyl)-iodonium
4-methyl-2,6-dioxocyclohexan-1-ylide

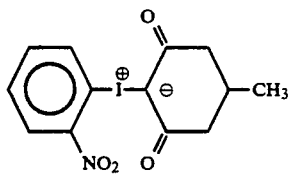

2-Nitroiodosobenzene (1.81 g, 6.8 mmol) and dichloromethane (70 mL) were stirred at room temperature to produce an orange colored mixture. 5-Methyl-1,3-cyclohexanedione (0.87 g, 6.9 mmol) was added as fine white crystalline spears to the dichloromethane mixture. Immediately, the reaction mixture color changed to yellow and was subsequently filtered in 20 min. The filtrate was evaporated at 35° C. in vacuo (aspirator) to give a medium yellow solid (2.1 g, 5.6 mmol, (82.8 percent) which was washed with acetonitrile (2×60 mL), filtered, and dried in vacuo (ca. 0.3 mm Hg) for 30 min to give title compound; yield, 0.78 g, 2.1 mmol, 30.7 percent; dec. 145° C. Product identification was based on PMR, CMR and elemental analysis.

| Analysis (elemental analysis) | | | |
|---|---|---|---|
| | C | H | N |
| Calc. for $C_{13}H_{11}INO_4$: | 41.96 | 2.97 | 3.76 |
| Found: | 42.00 | 3.30 | 3.67 |

EXAMPLE 16

(4-Methyl-2-nitrophenyl)-iodonium
2,2-dimethyl-4,6-dioxo-1,3-dioxan-5-ylide

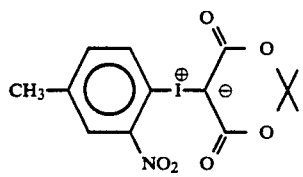

To a stirred solution of isopropylidene malonate (0.52 g, 3.6 mmol) and chloroform (20 mL) at 5° C. was added 1.0 g (3.6 mmol) of 2-nitro-4-methyl-iodosobenzene portion-wise over 15 min. As the orange iodoso compound was introduced, it was replaced by an insoluble green solid. When the addition was complete, the reaction mixture was kept in an ice-bath for 1 hr. The product, a light green solid, was isolated by filtration, a second crop being isolated from the filtrate, and identified by PMR analysis as the desired product; yield, 0.65 g; m.p. 185°–190° C. (dec).

EXAMPLE 17

(3,4-Dimethyl-2-nitrophenyl)-iodonium
2,2-dimethyl-4,6-dioxo-1,3-dioxan-5-ylide

To a stirred solution of isopropylidene malonate (0.49 g, 3.4 mmol) and chloroform cooled to

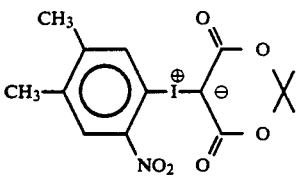

about 5° C., (20 mL) was added 1.0 g (3.4 mole) of 2-nitro-3,4-dimethyliodosobenzene portion-wise over 15 min. After an additional 30 min, a light green solid precipitate was isolated, washed with chloroform to give the desired product; yield, 0.85 g; m.p. 190°–193° C. (dec.).

EXAMPLE 18

(4-chloro-2-nitrophenyl)-iodonium
2,2-dimethyl-4,6-dioxo-1,3-dioxan-5-ylide

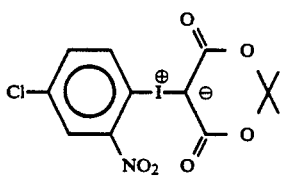

To a stirred cold (5° C.) solution of isopropylidenemalonate (0.41 g, 2.85 mmol) in chloroform (20 mL) was added 0.80 g (2.8 mmol) of 2-nitro-4-chloroiodosobenzene in portion-wise fashion over 45 min. Gradually, the insoluble, orange iodoso compound was replaced by a green solid. Since the orange compound was not completely consumed even after the addition was completed, more methanol (10 mL) and more isopropylidene malonate (0.1 g) were added, and the mixture was allowed to stir at 5° C. for 1.5 hr more. The insoluble component, a light green solid, was then isolated by filtration as the desired product; yield, 0.75 g, m.p. 182°–183° C.

EXAMPLE 19

(2-Nitrophenyl)-iodonium
2,2-dimethyl-4,6-dioxo-1,3-dioxan-5-ylide

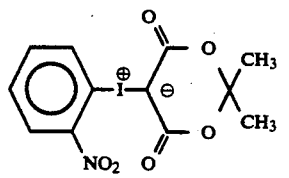

To a mixture of isopropylidene malonate (0.917 g) and 20 mL of chloroform was gradually added 1.78 g of o-nitroiodosobenzene. The resultant mixture was then stirred for about 15 min to give a precipitate which was then collected by filtration, washed with diethyl ether, and then air dried to give 1.88 g of desired product as a light yellow powder; m.p. 166°–168° C.

EXAMPLE 20

(4-Methoxy-2-nitrophenyl)-iodonium
2,2-dimethyl-4,6-dioxo-1,3-dioxan-5-ylide

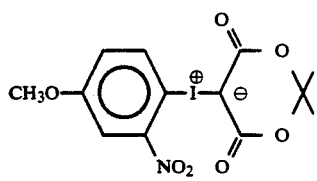

A procedure similar to that of Example 19 was repeated substituting 4-methoxy-2-nitroiodosobenzene for the o-nitroiodosobenzene.

The structure of the product was confirmed by PMR and elemental analysis.

EXAMPLE 21

((2-Methylsulfonyl)phenyl)-iodonium
2,2-dimethyl-4,6-dioxo-1,3-dioxan-5-ylide

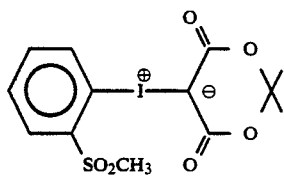

To a hot solution of O-methylsulfonyliodosobenzene (0.693 mmole, 200 mg) and 10 mL of methanol was added 100 mg (0.693 mmol) of Meldrum's acid. The resultant solution was allowed to cool in a freezer overnight during which time a precipitate was filtered which was dried under vacuum and determined by PMR and CMR to be the desired product; yield 210 mg; m.p. 165° C. (dec.).

| Analysis (elemental analysis) | | |
|---|---|---|
| | C | H |
| Calc. for $C_{13}H_{13}IO_6S$: | 36.81 | 3.09 |
| Found: | 37.00 | 3.23 |

EXAMPLE 22

(2-Nitrophenyl)-iodonium
6-fluoro-3,4-dihydro-2,4-dioxo-2H-benzopyran-3-ylide

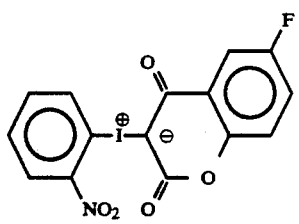

6-Fluoro-4-hydroxycoumarin (1 mmol, 180 mg) was dissolved in 7 mL of hot methanol and to it was added a solution of 2-nitroiodosobenzene (1 mmol, 265 mg) in 50 mL of hot methanol. The resultant solution was cool and a precipitate was formed. The precipitate was filtered, dried under vacuum and determined by both PMR and mass spectrometry (MS) to be the desired product; yield, 320 milligrams (mg); m.p. 190° C. (dec.).

| Analysis (elemental analysis) | | | |
|---|---|---|---|
| | C | H | N |
| Calc. for $C_{15}H_7O_5NFI$: | 42.18 | 1.65 | 3.27 |
| Found: | 42.10 | 1.81 | 3.14 |

EXAMPLE 23

(2-Nitrophenyl)-iodonium
6-bromo-3,4-dihydro-2,4-dioxo-2H-benzopyran-3-ylide

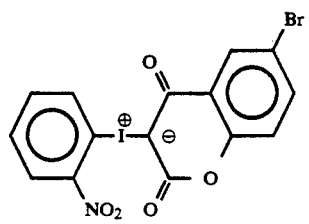

6-Bromo-4-hydroxycoumarin (1 mmol, 240 mg) was dissolved in 10 mL of hot methanol and to it was added a solution of 2-nitroiodosobenzene (1 mmol, 265 mg) in 15 mL of hot methanol. The resultant solution was allowed to cool and a precipitate was formed which was filtered, dried under vacuum and determined by both PMR and MS to be the desired product; yield, 390 mg; m.p. 288°–290° C. (dec.).

| Analysis (elemental analysis) | | | |
|---|---|---|---|
| | C | H | N |
| Calculated: | 36.91 | 1.44 | 2.87 |
| Found: | 36.90 | 1.75 | 2.74 |

EXAMPLE 24

(2-Nitrophenyl)-iodonium
6-chloro-3,4-dihydro-2,4-dioxo-2H-benzopyran-3-ylide

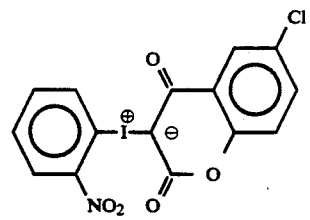

6-Chloro-4-hydroxycoumarin (1 mmol, 197 mg) was dissolved in 10 mL of hot methanol and to it was added a solution of 2-nitroiodosobenzene (1 mmol, 265 mg) in 15 mL of hot methanol. The resultant solution was allowed to cool and a precipitate was formed. The precipitate was filtered, dried under vacuum, and determined to be the desired product by CMR, PMR, MS; yield, 340 mg; m.p. 262°–265° C.

| Analysis (elemental analysis) | | | |
|---|---|---|---|
| | C | H | N |
| Calc. for $C_{15}H_7O_5NCII$: | 40.61 | 1.59 | 3.15 |
| Found: | 40.50 | 1.70 | 3.10 |

EXAMPLE 25

((2-Methylsulfonyl)phenyl)-iodonium 3,5-dihydro-2,4-dioxo-2H-benzopyran-3-ylide

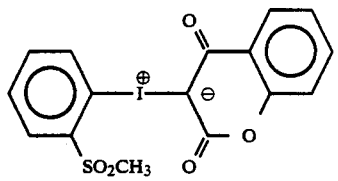

4-Hydroxycoumarin, (0.5 mmol, 80 mg) was dissolved in 5 mL of hot methanol and to the methanolic solution was added a solution of O-methylsulfonyliodosobenzene (0.5 mmol, 150 mg) and 10 mL of hot methanol. The resultant solution was allowed to cool down and a precipitate formed. The precipitate was filtered, dried under vacuum, and determined by PMR and CMR to be the desired product; yield, 170 mg; m.p. 168° C.

| | Analysis (elemental analysis) | |
|---|---|---|
| | C | H |
| Calc. for $C_{16}H_{11}IO_5S$: | 43.45 | 2.51 |
| Found: | 43.60 | 2.56 |

EXAMPLE 26

(2-Nitrophenyl)-iodonium 6-carboxy-3,4-diohydro-2,4-dioxo-2H-benzopyran-3-ylide

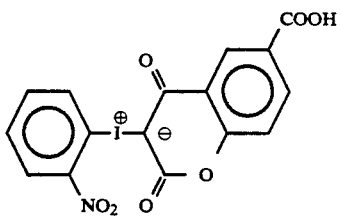

6-Carboxy-4-hydroxycoumarin (0.5 mmole, 102 mg) was dissolved in a 10 mL amount of hot methanol and to the solution was added a solution consisting of o-nitroiodosobenzene (0.5 mmol, 150 mg) and 15 mL of hot methanol. The resultant solution was allowed to cool, and a precipitate was formed which was filtered, dried under vacuum and determined by PMR and CMR to be the desired product; yield, 185 mg; m.p. 293°-294° C. (dec.).

| | Analysis (elemental analysis) | | |
|---|---|---|---|
| | C | H | N |
| Calc. for $C_{16}H_8INO_7$: | 42.41 | 1.78 | 3.09 |
| Found: | 41.10 | 2.06 | 2.90 |

EXAMPLE 27

((2-Methylsulfonyl)phenyl)-iodonium 6-chloro-3,4-dihydro-2,4-dioxo-2H-benzopyran-3-ylide

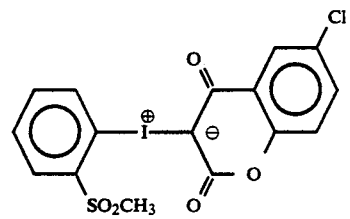

To a solution of O-methylsulfonyliodosobenzene (0.67 mmol, 200 mg) and 10 mL of methanol was added a solution of 6-chloro-4-hydroxycoumarin (0.67 mmole, 131 mg) and 10 mL of hot methanol. The resultant solution was cooled to give a precipitate which was filtered, dried under vacuum and determined by PMR, CMR and MS to be the desired product; yield, 220 mg; m.p. 279°-280° C. (dec.).

| | Analysis (elemental analysis) | |
|---|---|---|
| | C | H |
| Calc. for $C_{16}H_{10}ClIO_5S$: | 40.31 | 2.11 |
| Found: | 40.20 | 2.26 |

EXAMPLE 28

((2-Methylsulfonyl)phenyl)-iodonium 3,4-dihydro-6-methoxy-2,4-dioxo-2H-benzopyran-3-ylide

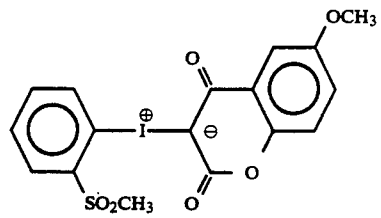

To a solution of O-methylsulfonyliodosobenzene (0.67 mmole, 200 mg) and 10 mL of hot methanol was added a solution consisting of 6-methoxy-4-hydroxycoumarine (0.67 mmole, 129 mg) and 15 mL of hot methanol. After cooling, the resultant solution was filtered free of a precipitate which was dried under vacuum and determined by PMR to be the desired product; yield, 220 mg; m.p. 270°-272° C. (dec.).

| | Analysis (elemental analysis) | |
|---|---|---|
| | C | H |
| Calc. for $C_{17}H_{13}IO_6S$: | 43.24 | 2.77 |
| Found: | 43.00 | 2.94 |

EXAMPLE 29

((2-Methylsulfonyl)phenyl)-iodonium 6-carboxy-3,4-dihydro-2,4-dioxo-2H-benzopyran-3-ylide

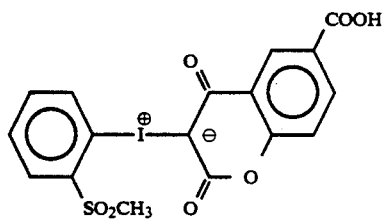

To a solution of O-methylsulfonyliodosobenzene (0.67 mmol, 200 mg) and 10 mL of methanol was added a solution consisting of 6-carboxy-4-hydroxycoumarin (0.78 mmol, 138 mg) and 10 mL of hot methanol. The resultant solution was cooled to give a precipitate which was filtered, dried under vacuum and determined by CMR, PMR and MS to be the desired product: yield, 210 mg: m.p. 278°–280° C. (dec.).

| Analysis (elemental analysis) | | |
|---|---|---|
| | C | H |
| Calc. for $C_{17}H_{11}IO_7S$: | 41.99 | 2.28 |
| Found: | 42.00 | 2.40 |

EXAMPLE 30

((2-Methylsulfonyl)phenyl)-iodonium 6-bromo-3,4-dihydro-2,4-dioxo-2H-benzopyran-3-ylide

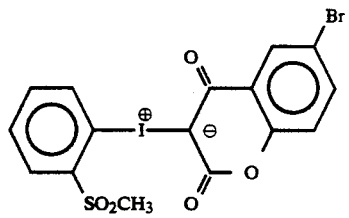

To a solution of O-methylsulfonyliodosobenzene (0.5 mol, 150 mg) and 10 mL of hot methanol was added to a solution consisting of 6-bromo-4-hydroxycoumarin (0.5 mmol, 120 mg) and 15 mL of hot methanol. The resultant solution was cooled to give a precipitate which was filtered, dried under vacuum, and determined by PMR, CMR and MS to be the desired product: yield, 180 mg: m.p. 285°–287° C. (dec.).

| Analysis (elemental analysis) | | |
|---|---|---|
| | C | H |
| Calc. for $C_{16}H_{10}BrIO_5S$: | 36.88 | 1.93 |
| Found: | 36.70 | 2.08 |

EXAMPLE 31

((2-Methylsulfonyl)phenyl)-iodonium 6-fluoro-3,4-dihydro-2,4-dioxo-2H-benzopyran-3-ylide

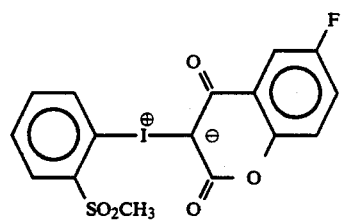

6-Fluoro-4-hydroxycoumarin (0.5 mmol, 90 mg) was dissolved in 7 mL of hot methanol and to the solution was added a solution consisting of iodosophenyl-2-methylsulfone (0.5 mmole, 150 mg) and 10 mL of hot methanol. The resultant solution was cooled to give a precipitate which was filtered, dried under vacuum, and determined to be the desired product; yield, 173 mg; m.p. 176° C. (dec.).

| Analysis (elemental analysis) | | |
|---|---|---|
| | C | H |
| Calc. for $C_{16}H_{10}FIO_5S$: | 41.76 | 2.19 |
| Found: | 41.60 | 2.35 |

EXAMPLE 32

(2-Nitrophenyl)-iodonium 3,4-dihydro-2,4-dioxo-2H-benzopyran-3-ylide

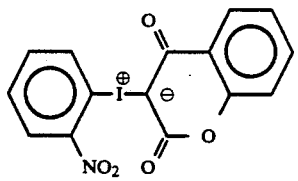

4-Hydroxycoumarin (1.00 g, 6.17 mmole) was dissolved in 100 mL of boiling ethylacetate. The resultant solution was cooled to 25° C. and o-nitroiodosobenzene (1.40 g, 5.29 mmole) was added to this solution to give an orange colored suspension which was stirred vigorously for 1 hr. The color gradually changed from orange to yellow as the desired product precipitated from solution. The yellow material was filtered, and vacuum dried to give 1.50 g of the desired compound as a light yellow powder in 69 percent yield; m.p. 161°–161.5° C. The structure was confirmed by PMR, CMR and MS.

| Analysis (elemental analysis) | | | |
|---|---|---|---|
| | C | H | N |
| Calc. for $C_{15}H_8INO_5$: | 44.03 | 1.97 | 3.42 |
| Found: | 43.60 | 1.98 | 3.48 |

EXAMPLE 33

(2-Nitrophenyl)-iodonium 3,4-dihydro-6-methoxy-2,4-dioxo-2H-benzopyran-3-ylide

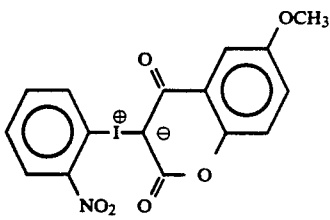

6-Methoxy-4-hydroxycoumarin (800 mg, 4.17 mmol was dissolved in 125 mL of boiling methanol with stirring. The resultant solution was cooled to 25° C. and o-nitroiodosobenzene (1.10 g, 4.15 mmol) was added with stirring the mixture for 20 min during which time a bright yellow precipitate (1.3 g, 71 percent yield) formed which was filtered and vacuum dried; m.p. 198° C. The structure was confirmed by NMR, CMR and MS characterization.

| Analysis (elemental analysis) | | | |
|---|---|---|---|
| | C | H | N |
| Calc. for $C_{16}H_{10}O_6IN$: | 43.76 | 2.30 | 3.19 |
| Found: | 43.70 | 2.42 | 2.99 |

EXAMPLE 34

(2-Nitrophenyl)-iodonium 3,4-dihydro-8-methyl-2,4-dioxo-2H-benzopyran-3-ylide

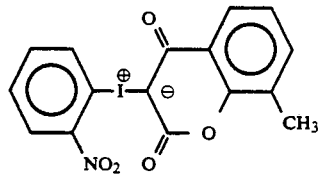

8-Methyl-4-hydroxycoumarin (600 mg, 3.41 mmole) was dissolved in 150 mL of boiling methanol. After cooling the solution to 25° C., 900 mg of finely powdered o-nitroiodosobenzene was added with vigorous stirring. The resultant orange colored solution turned light yellow immediately and a fine, white precipitate formed. The solution was stirred for 30 min more and the precipitate was filtered and dried to give the desired product which was characterized PMR, CMR and MS analysis; yield, 1.2 g; m.p. 265°–267° C. (dec).

| Analysis (elemental analysis) | | | |
|---|---|---|---|
| | C | H | N |
| Calc. for $C_{16}H_{10}INO_5$: | 45.39 | 2.36 | 3.31 |
| Found: | 45.40 | 2.48 | 3.20 |

EXAMPLE 35

(2-Nitrophenyl)-iodonium 3,4,5,6-tetrahydro-4,6-doxo-5-pyrimidinylide

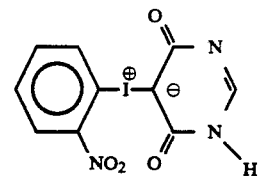

4,6-Dihydroxypyrimidine, (1 mmol, 112 mg) was dissolved in about 60 mL of hot methanol and to this was added a solution of o-nitrophenyliodoso benzene (1 mmol, 265 mg) and allowed to cool in a freezer at about −12° C. for about 48 hr. The resultant crystals were collected by filtration and dried under vacuum and determined by PMR to be the desired product; yield 230 mg; m.p. 206° C. (dec.).

| Analysis (elemental analysis) | | | |
|---|---|---|---|
| | C | H | N |
| Calc. for $C_{10}H_7IN_3O_4$: | 33.45. | 1.68 | 11.70 |
| Found: | 34.00 | 1.87 | 12.36 |

EXAMPLE 36

(2-Nitrophenyl)-iodonium 1,3-diethylhexahydro-4,6-dioxo-2-thiopyrimidin-5-ylide

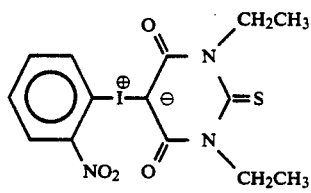

1,3-Diethyl-2-thiobarbituric acid (1 mmol, 200 mg) was dissolved in 5 mL of hot methanol and to it was added a solution of o-nitrophenyliodosobenzene (1 mmol, 265 mg) in 15 mL hot methanol. The resulting solution was allowed to stand overnight during which time crystals formed. The crystals were filtered and dried under vacuum and determined by PMR to be the desired product: yield, 252 mg: m.p. 210° C.

EXAMPLE 37

((2-Methylsulfonyl)phenyl)-iodonium 1,3-diethylhexahydro-4,6-dioxo-2-thiopyrimidin-5-ylide

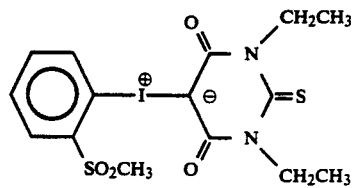

1,3-Diethyl-2-thiobarbituric acid (0.69 mmol, 130 mg), obtained from Aldrich, was dissolved in 5 mL of hot methanol and to it was added a solution of 2-methylsulfonyliodosobenzene (0.67 mmol, 200 mg) in 10 mL of hot methanol. After the addition, crystals were formed which were filtered and dried under vacuum and determined to be the desired product: yield 160 mg.

| Analysis (elemental analysis) | | | |
|---|---|---|---|
| | C | H | N |
| Calc. for $C_{14}H_{17}N_2O_4SI$: | 38.54 | 3.93 | 6.42 |
| Found: | 38.40 | 3.52 | 9.68 |

EXAMPLE 38

((2-Methylsulfonyl)phenyl)-iodonium 3,4,5,6-tetrahydro-4,6-dioxopyrimidin-5-ylide

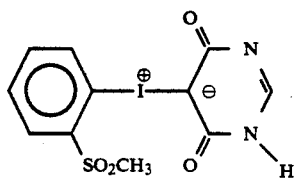

2,4-Dihydroxypyrimidine (75 mg. 0.67 mmole) was dissolved in 70 mL of hot methanol and to it was added a solution of 2-(methylsulfonyl)iodosobenzene (200 mg, 0.67 mmole) with stirring. The resultant solution was concentrated to 25 mL and the desired crystalline ylide was filtered and dried. The product was characterized by PMR; yield, 170 mg; m.p. 238°-240° C. (dec).

| Analysis (elemental analysis) | | | |
|---|---|---|---|
| | C | H | N |
| Calc. for $C_{11}H_9N_2IO_4S$: | 33.69 | 2.31 | 7.15 |
| Found: | 33.25 | 2.59 | 6.81 |

EXAMPLE 39

((2-Methylsulfonyl)phenyl)-iodonium hexahydro-2,4,6-trioxopyrimidin-5-ylide

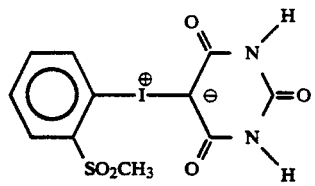

To a solution of O-methylsulfonyliodosobenzene (0.67 mmol, 200 mg) and 10 mL of hot methanol was added a solution consisting of barbituric acid (0.67 mol, 86 mg) and 5 mL of hot methanol. A precipitate formed immediately which was filtered, dried under vacuum and determined by PMR to be the desired product; yield, 230 mg; m.p. 241°-243° C. (dec.).

| Analysis (elemental analysis) | | | |
|---|---|---|---|
| | C | H | N |
| Calc. for $C_{11}H_9IN_2O_5S$: | 32.37 | 2.22 | 6.86 |
| Found: | 31.10 | 2.38 | 6.52 |

EXAMPLE 40

((2-Methylsulfonyl)phenyl)-iodonium 1,2,3,4-tetrahydro-2,4-dioxoquinolin-3-ylide

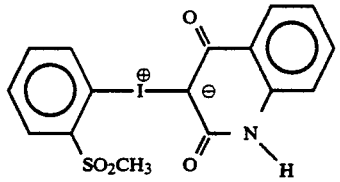

2,4-Quinolinediol (0.67 mmole, 108 mg) was dissolved in hot methanol (~70 mL) and to this solution was added a solution of O-methylsulfonyliodosobenzene (0.67 mmol, 200 mg) and 10 mL of hot methanol. The resultant solution was allowed to cool to give a precipitate which was filtered, dried under vacuum and determined to be the desired product; yield, 230 mg; m.p. >300° C.

| Analysis (elemental analysis) | | | |
|---|---|---|---|
| | C | H | N |
| Calc. for $C_{16}H_{12}INO_4S$: | 43.55 | 2.74 | 3.18 |
| Found: | 43.30 | 3.02 | 3.08 |

EXAMPLE 41

(2-Nitrophenyl)-iodonium 1,2,3,4-tetrahydro-2,4-dioxoquinolin-3-ylide 2,4-Quinoline diol (323 mg, 2.02 mmole) was dissolved in 75 mL of methanol. o-Nitroiodosobenzene (531 mg, 2.00 mmole) in 75 mL of methanol was added to the diol solution at 30° C. with stirring. The resultant light yellow precipitate was filtered, washed with 15 mL of cold methanol and dried in vacuo (about 1 mm Hg) to give desired ylide which was identified by PMR and MS; yield, 680 mg; m.p. 281° C. (dec) (noted yellow to white color change at 194° C.).

| Analysis (elemental analysis) | | | |
|---|---|---|---|
| | C | H | N |
| Calc. for $C_{15}H_9O_4N_2I$: | 44.14 | 2.22 | 6.86 |
| Found: | 43.90 | 2.12 | 6.74 |

EXAMPLE 42

((2-Methylsulfonyl)phenyl)-iodonium 1,2,3,4-tetrahydro-2,4-dioxopyridine3-ylide

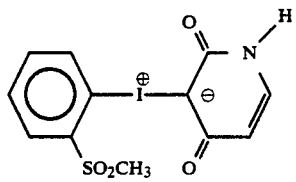

To a solution of 2,4-dihydroxypyridine (0.67 mmol, 73 mg) and 10 mL of hot methanol was added a solution of O-methylsulfonyliodosobenzene (0.67 mmol, 200 mg) and 10 mL of hot methanol. The resultant solution was cooled in the freezer at about −12° C. for about 2 hr. The resultant precipitate was collected by filtration, dried under vacuum, and determined by PMR and CMR to be the desired product; yield, 170 mg; m.p. 252°–256° C. (dec.).

| Analysis (elemental analysis) | | | |
|---|---|---|---|
| | C | H | N |
| Calc. for $C_{11}H_{10}INO_4S$: | 34.84 | 2.66 | 3.69 |
| Found: | 35.40 | 2.70 | 3.38 |

EXAMPLE 43

(2-Nitrophenyl)-iodonium 1,2,3,4-tetrahydro-2,4-dioxopyridin-3-ylide

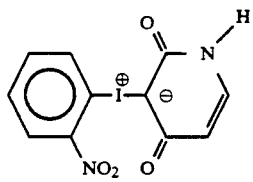

To a solution of 2,4-dihydroxypyridine (1 mmol, 111 mg) was dissolved and 10 mL of hot methanol was added to a solution of 2-nitroiodosobenzene (1 mmol, 265 mg) and 15 mL of hot methanol. The resultant solution was cooled in the freezer at about −12° C. for about 2 hr to give a precipitate which was collected by filtration, dried under vacuum, and determined by PMR and CMR to be the desired product; yield, 220 mg; m.p. 247°–249° C. (dec.).

| Analysis (elemental analysis) | | | |
|---|---|---|---|
| | C | H | N |
| Calc. for $C_{11}H_7IN_2O_4$: | 36.89 | 1.97 | 7.87 |
| Found: | 36.10 | 2.12 | 7.59 |

EXAMPLE 44

(2-Nitrophenyl)-iodonium hexahydro-2,4,6-trioxo-5-pyrimidin-1-ylide

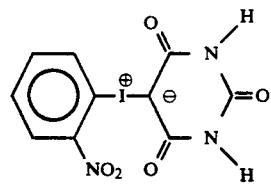

Barbituric acid (256 mg, 2.00 mmole) was dissolved in 25 mL of hot methanol. A mixture of o-nitroiodosobenzene (540 mg, 2.04 mmole) and 25 mL of methanol was added with stirring to the barbituric acid solution. A white precipitate developed immediately which was filtered and dried to yield the desired product which was characterized by NMR and MS; yield, 700 mg; m.p. 250°–257° C.

| Analysis (elemental analysis) | | | |
|---|---|---|---|
| | C | H | N |
| Calc. for $C_{10}H_6O_5N_3I$: | 32.00 | 1.61 | 11.20 |
| Found: | 31.50 | 1.40 | 10.95 |

EXAMPLE 45

(2-Nitrophenyl)-iodonium hexahydro-2,4,6-trioxopyrimidin-5-ylide hydrate

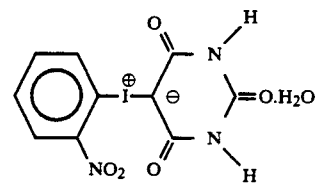

Structure was confirmed by PMR and elemental analysis. Melting point range was no greater than 5° C.

EXAMPLE 46

((2-Methylsulfonyl)phenyl)-iodonium 3,4-dihydro-6-methyl-2,4-dioxo-2H-pyran-3-ylide

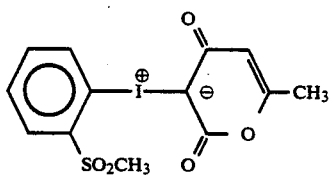

4-Hydroxy-6-methyl-2-oxo-2H-pyran (85 mg, 0.67 mmol) was added to a hot solution of o-methylsulfonyliodosobenzene (200 mg, 0.67 mmol) and 10 mL of methanol. After cooling the resultant solution, the desired product precipitated, which was filtered, dried under vacuum and characterized by PMR and CMR; yield, 198 mg; m.p. 165° C. (dec.).

| Analysis (elemental analysis) | | |
| --- | --- | --- |
| | C | H |
| Calc. for $C_{13}H_{11}IO_5S$: | 38.11 | 2.73 |
| Found: | 37.90 | 2.50 |

EXAMPLE 47

(2-Nitrophenyl)-iodonium 3,4-dihydro-6-methyl-2,4-dioxo-2H-pyran-3-ylide

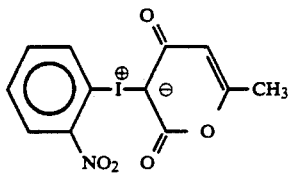

To a solution of 4-hydroxy-7-methylpyrone (252 mg, 2.00 mmol) and 25 mL of methanol was added a mixture of o-nitroiodosylbenzene (533 mg, 2.01 mmol) and 30 mL of methanol with stirring. The first crop of desired product (332 mg) was obtained as a light yellow solid (m.p. 162°-162.5° C.). Evaporation of the mother liquor afforded a second crop of desired product (280 mg) (m.p. 160°-162° C) to afford a total yield of 81 percent. The title compound was characterized by PMR, CMR and MS.

| Analysis (elemental analysis) | | | |
| --- | --- | --- | --- |
| | C | H | N |
| Calc. for $C_{12}H_8NO_5I$: | 38.61 | 2.17 | 3.75 |
| Found: | 39.00 | 2.16 | 3.60 |

EXAMPLE 48

(2-Nitrophenyl)-iodonium 2,3-dihydro-1,3-dioxo-1H-indan-2-ylide

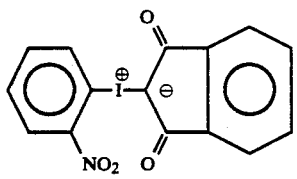

A mixture of o-iodosonitrobenzene (2.45 g) and dichloromethane (50 mL) were stirred at 25° C. and to the resultant orange colored mixture was added 1,3-indandione (1.35 g). The reaction mixture then turned a deep red color followed by a change to a rich yellow color. The dichloromethane solvent was then evaporated to give a yellow solid which was washed with water (2×75 mL), filtered, further rinsed with methyl t-butyl ether (2×20 mL) and air dried to afford a yellow solid which was identified by PMR and CMR as the desired product; yield, (1.2 g); m.p. 110°-120° C. (dec).

| Analysis (elemental analysis) | | | | |
| --- | --- | --- | --- | --- |
| | C | H | N | I |
| Calc. for $C_{15}H_8INO_4$: | 45.83 | 2.05 | 3.56 | 32.28 |
| Found: | 43.64 | 2.35 | 3.40 | 31.00 |

EXAMPLE 49

(2-Nitrophenyl-)-iodonium-2,3,4,5-tetrahydro-2,4-dioxo-furan-3-ylide

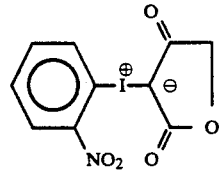

Tetronic acid (330 mg, 3.1 mmole) and 2-nitroiodosobenzene (795 mg, 3.00 mmole) were added to 20 mL of acetonitrile. Within 20 min, the white precipitate was filtered and dried to afford desired ylide which was characterized by PMR, CMR and MS; yield, 700 mg; m.p. 135°-136° C. (dec).

| Analysis (elemental analysis) | | | |
| --- | --- | --- | --- |
| | C | H | N |
| Calc. for $C_{10}H_6O_5NI$: | 34.60 | 1.74 | 4.03 |
| Found: | 34.00 | 1.74 | 4.02 |

EXAMPLE 50

((2-Nitro-4-methoxy)phenyl)-iodonium 3,4-dihydro-6-methyl-2,4-dioxo-2H-pyran-3-ylide

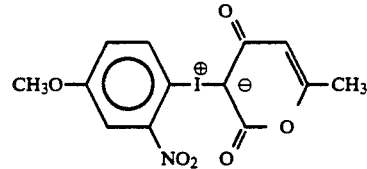

To a stirred mixture of 4-hydroxy-7-methylpyrone (0.264, 2.09 mmol) in chloroform (10 mL), warmed slightly, was added 0.5929 (2.01 mmol) of the bright red-orange 2-nitro-4-methoxy-iodosobenzene powder. Within several min the mixture cleared to a yellow solution and within several more min, the solution developed with a thick yellow precipitate. After about 30 min, the reaction mixture was diluted with chloroform and the yellow insoluble solid was isolated by filtration. Washes with chloroform and then ether followed by air drying provided a very pale yellow "fibrous" powder (yield, 0.411 g) which darkens before it melted at 165°-167° C. A second crop of 0.159 g of product separated from the chloroform/diethyl ether mother liquor as a golden yellow microcrystalline solid with a m.p. 170°-172° C (dec to black liq.).

The stability of the compounds of Formula I was demonstrated by the ability to perform elemental analyses on the compounds, the conditions under which many of the compounds were subjected (i.e., hot methanol), and the small range of melting points determined to exist for the compounds.

The antimicrobial activity of the compounds of Formula I was demonstrated by the following techniques.

The minimum inhibitory concentration (MIC) for the compound of Example 19, i.e., (2-nitrophenyl)-iodonium 2,2-dimethyl-4,6-dioxo-1,3-dioxan-5-ylide was determined for 9 bacteria (using nutrient agar) and 5 yeast and fungi (using malt yeast agar). A one percent solution of this test compound (i.e., the compound of Example 19) was prepared in a mixture of acetone-water. Nutrient agar was prepared at pH 6.8 using deionized water according to standard Difco procedures. Malt yeast agar was prepared by adding 3 g Bacto yeast extract and 42 g Bacto Malt agar per liter of deionized water. The agar (nutrient agar when testing with bacteria and malt yeast agar when testing with yeast and fungi) was dispensed in 30 mL aliquots into 25×200 millimeter (mm) test tubes, capped and autoclaved for 15 min at 115° C. The test tubes containing the agar were cooled in a water bath until the temperature of the agar was 48° C. and then an appropriate amount of the one percent solution of the test compound was added (except in the controls where no test compound was added with the acetone-water) to the respective test tubes so that final concentrations of 500, 250, 100, 50, 25, 10, 5, 2.5, 1.0 and 0 parts per million (ppm) of the test compound in the agar were obtained. The agar solutions were each mixed and poured into individual petri plates so that each petri plate contained agar having a known concentration of test compound dispersed therein. After drying for 24 hr, the petri plates were inoculated with bacteria when the petri plates contained nutrient broth agar or with fungi and yeast when the petri plates contained malt yeast agar.

The inoculation with bacteria was accomplished using the following procedure. Twenty-four hr cultures of each of the bacteria were prepared by incubating the respective bacteria in tubes containing nutrient broth for 24 hr at 30° C. in a shaker. Dilutions of each of the 24 hr cultures were made so that 9 separate suspensions (one for each of the 9 test bacteria) were made, each containing about $10^8$ colony forming units (CFU) per mL of suspension of a particular bacteria. Aliquots of 0.3 mL of each of the above suspensions were used to fill individual wells of a Steer's Replicator. For each microbial suspension, 0.3 mL was used to fill 3 wells (i.e., 3 wells of 0.3 mL each) so that for the 9 different bacteria 27 wells were filled. The Steer's Replicator was then used to inoculate the petri plates.

The petri plates were incubated at 30° C. for 48 hr and then read to determine if the test compound (i.e., the compound of Example 19) which was incorporated into the agar prevented growth of the respective bacteria. The minimum inhibitory concentration (MIC) for each bacteria was defined as the lowest concentration of the test compound which prevented growth of that bacteria.

The inoculation with the fungi and yeast was accomplished as follows. Cultures of fungi and yeast were incubated for 7 days on malt yeast agar at 30° C. These cultures were used to prepare suspensions by the following procedure. A suspension of each organism was prepared by adding 10 mL of sterile saline and 10 microliters (mL) of Triton ×100 to the slant. The sterile saline/Triton ×100 solution was then agitated with a sterile swab to suspend the microorganism grown on the slant. Each resulting suspension was diluted into sterile saline (1 part suspension: 9 parts sterile saline). Aliquots of these dilutions were placed in individual wells of a Steer's Replicator and petri plates inoculated as previously described. The petri plates were incubated at 30° C. and read after 48 hr for yeast and 72 hr for fungi.

Table 1 sets forth the MIC (in ppm) of (2-Nitrophenyl)-iodonium 2,2-dimethyl-4,6-dioxo-1,3--dioxan-5-ylide for the organisms shown therein.

TABLE 1

| Organism | ATCC # | MIC ((2-nitrophenyl)-iodonium 2,2-dimethyl-4,6-dioxo-1,3-dioxan-5-ylide) |
|---|---|---|
| Bacillus subtilis | 8473 | ≦1.0 |
| Enterobacter aerogenes | 13048 | 1.0 |
| Escherichia coli | 11229 | ≦1.0 |
| Klebsiella pneumoniae | 8308 | ≦1.0 |
| Proteus vulgaris | 881 | ≦1.0 |
| Pseudomonas aeruginosa | 10145 | 10.0 |
| Pseudomonas aeruginosa PRD-10 | 15442 | 10.0 |
| Salmonella choleraesuis | 10708 | ≦1.0 |
| Staphylococcus aureus | 6538 | ≦1.0 |
| Aspergillus niger | 16404 | 250.0 |
| Penicillium chrysogenum | 9480 | 100.0 |
| Trichoderma viride | 8678 | 250.0 |
| Candida albicans | 10231 | 100.0 |
| Saccharomyces cervisiae | 4105 | 100.0 |

In a similar procedure, the MIC (in ppm) of the compound of Example 11 (i.e., (2-nitrophenyl)-iodonium 2,6-dioxocyclohexylide) for various organisms was determined at an acid pH (about 6.8) and at an alkaline pH (about 8.2). The results are shown in Table 2.

TABLE 2

| | | MIC - Example 1 | |
|---|---|---|---|
| Organism | ATCC # | Neutral Medium | Alkaline Medium |
| Bacillus subtilis | 8473 | ≦1.0 | ≦1.0 |
| Enterobacter aerogenes | 13048 | ≦1.0 | ≦1.0 |
| Escherichia coli | 11229 | ≦1.0 | ≦1.0 |
| Klebsiella pneumoniae | 8308 | ≦1.0 | ≦1.0 |
| Proteus vulgaris | 881 | ≦1.0 | ≦1.0 |
| Pseudomonas aeruginosa | 10145 | ≦1.0 | ≦1.0 |
| Pseudomonas aeruginosa PRD-10 | 15442 | ≦1.0 | ≦1.0 |
| Salmonella choleraesuis | 10708 | ≦1.0 | ≦1.0 |
| Staphylococcus aureus | 8538 | ≦1.0 | ≦1.0 |

Using similar procedures, the MIC's (in ppm) of various compounds of Formula I and/or Formula II were determined for the organisms *Enterobacter aerogenes* and *Bacillus subtilis* in a neutral solution (pH about 6.8) and in an alkaline medium (pH about 8.2). Results of selected compounds are set forth in Table 3.

TABLE 3

| Compound Example No. | NBS[a] | ABS[b] | NEA[c] | AEA[d] |
|---|---|---|---|---|
| 10 | 25 | >500 | ≦10 | >500 |
| 16 | 2.5 | 5 | 2.5 | 10 |
| 17 | <10 | <10 | 25 | 25 |
| 22 | ≦10 | 100 | ≦10 | 250 |
| 23 | 100 | 250 | >500 | >500 |
| 35 | 250 | >500 | 100 | >500 |
| 26 | ≦10 | 250 | 250 | 250 |
| 21 | 25 | 50 | >500 | >500 |
| 27 | ≦10 | ≦10 | >500 | >500 |
| 46 | ≦10 | ≦10 | 100 | 50 |
| 28 | ≦10 | ≦10 | >500 | >500 |
| 29 | ≦10 | ≦10 | >500 | >500 |
| 30 | ≦10 | ≦10 | >500 | >500 |
| 35 | ≦10 | ≦10 | >500 | >500 |
| 43 | 50 | 500 | 500 | >500 |
| 42 | 500 | 500 | 500 | >500 |
| 32 | ≦10 | ≦10 | ≦10 | 25 |
| 33 | ≦10 | ≦10 | >500 | >500 |
| 36 | >500 | >500 | 500 | >500 |
| 12 | 250 | 100 | >500 | >500 |
| 47 | 25 | 500 | 100 | 500 |
| 18 | 100 | 250 | 100 | 250 |
| 48 | ≦1 | 25 | 50 | 250 |
| 14 | 2.5 | ≦1 | 2.5 | ≦1 |

TABLE 3-continued

| Compound Example No. | NBS[a] | ABS[b] | NEA[c] | AEA[d] |
|---|---|---|---|---|
| 15 | ≦10 | ≦10 | ≦10 | 100 |
| 44 | 100 | >500 | 100 | 500 |
| 34 | ≦10 | 25 | 500 | 500 |
| 41 | ≦10 | 500 | ≦10 | >500 |
| 45 | 100 | >500 | 100 | 500 |
| 20 | ≦10 | 25 | ≦10 | 25 |

[a]*Bacillus subtilis* in neutral growth medium (pH = 6.8)
[b]*Bacillus subtilis* in alkaline growth medium (pH = 8.2)
[c]*Enterobacter aerogenes* in neutral growth medium (pH = 6.8)
[d]*Enterobacter aerogenes* in alkaline growth medium (pH = 8.2)

The ability of the compounds of Formula I to serve as preservatives (as demonstrated by the use of (2-nitrophenyl)-iodonium 2,2-dimethyl-4,6-dioxo-1,3-dioxan-5-ylide) was tested both in latex and cutting oil emulsions. The latex was a vinylidene chloride-butadiene copolymer with a pH of 6.1. The emulsion type cutting oil was a concentrate, Vantrol ® 51-086-B, manufactured by Van Straaten Chemical Company; this concentrate was diluted 1:40 with tap water and had a final pH of 9.7.

Fifty gram aliquots of the latex were placed in sterile bottles and one hundred gram aliquots of the diluted cutting oil were placed in 250-mL Erlenmeyer flasks. An appropriate amount of a fresh 1 percent stock solution of (2-nitrophenyl)-iodonium 2,2-dimethyl-4,6-dioxo-1,3-dioxan-5-ylide in acetone-water was added to achieve the desired final concentrations (see Tables 5 and 6). A small portion of the respective latex or cutting oil preparation was then streaked onto Tryptic Soy Agar (TSA) petri plates using sterile cotton swabs to determine whether the preparations were sterile. If the particular preparation was sterile, it was then inoculated with an appropriate volume (0.1 mL for the latex and 0.2 mL for the cutting oil) of a mixture of equal aliquots of 24 hr cultures of each of the bacterial organisms listed in Table 1 (not the fungi and yeast). The latex samples were incubated at 30° C. and the cutting oils were agitated on a rotary shaker at room temperature. After 24 hr, all samples were again streaked on TSA. All plates were then incubated at 30° C. for 48 hr and then rated 1 to 10 according to the growth rating system described in Table 4.

TABLE 4

| GROWTH RATING | |
|---|---|
| Rating | No. of Colonies |
| 1 | 0 |
| 2 | 1-4 |
| 3 | 5-10 |
| 4 | 11-25 |
| 5 | 26-50 |
| 6 | 51-100 |
| 7 | 101-200 |
| 8 | 210-300 |
| 9 | Too many to count |
| 10 | Solid Mass |

The results from this first set of streaks after inoculation are listed in the columns labeled streak number 1 in Tables 5 and 6. Samples with a rating of 3 or less from streak number 1 were reinoculated as described for the first inoculation above. Samples with a rating of 4 or greater were not reinoculated. After another 24 hr all samples were again restreaked on TSA agar. The results from these second streaks were labeled streak number 2 in Tables 5 and 6. Samples were reinoculated and restreaked in this fashion for a maximum of 10 streaks. Any samples with two streaks in a row with a ten rating were not restreaked again.

TABLE 5

| | LATEX PRESERVATION TEST[a] | | | | | | | | | |
|---|---|---|---|---|---|---|---|---|---|---|
| Conc. | Streak Number | | | | | | | | | |
| (ppm) | 1 | 2 | 3 | 4 | 5 | 6 | 7 | 8 | 9 | 10 |
| 1000 | 1 | 1 | 1 | 1 | 1 | 1 | 1 | 1 | 1 | 1 |
| 500 | 1 | 1 | 1 | 1 | 1 | 1 | 1 | 1 | 1 | 1 |
| 250 | 1 | 1 | 1 | 1 | 1 | 1 | 1 | 1 | 1 | 1 |
| 100 | 1 | 2 | 1 | 1 | 1 | 1 | 1 | 1 | 1 | 1 |
| 50 | 1 | 2 | 1 | 1 | 1 | 1 | 1 | 1 | 1 | 1 |
| 25 | 1 | 9 | 1 | 1 | 1 | 1 | 1 | 1 | 2 | 2 |
| 10 | 1 | 1 | 1 | 1 | 6 | 10 | 10 | 10[b] | | |
| 5 | 6 | 1 | 7 | 10 | 10 | 10[b] | | | | |

[a]The values shown represent the growth rating obtained (see Table 4) for each particular challenge when (2-nitrophenyl)-iodonium 2,2-dimethyl-4,6-dioxo-1,3-dioxan-5-ylide was present at the indicated concentration.
[b]Restreaking was not continued.

TABLE 6

| | CUTTING OIL PRESERVATION TEST[a] | | | | | | | | | |
|---|---|---|---|---|---|---|---|---|---|---|
| Conc. | Streak Number | | | | | | | | | |
| (ppm) | 1 | 2 | 3 | 4 | 5 | 6 | 7 | 8 | 9 | 10 |
| 1000 | 1 | 1 | 1 | 1 | 1 | 1 | 1 | 1 | 1 | 1 |
| 500 | 1 | 1 | 1 | 1 | 1 | 1 | 1 | 1 | 1 | 1 |
| 250 | 1 | 1 | 1 | 1 | 1 | 1 | 1 | 1 | 6 | 10 |
| 100 | 1 | 2 | 2 | 1 | 10 | 10[b] | | | | |
| 50 | 1 | 2 | 10 | 10[b] | | | | | | |
| 25 | 1 | 9 | 10 | 10[b] | | | | | | |

[a]The values shown represent the growth rating obtained (see Table 4) for each particular challenge when (2-nitrophenyl)-iodonium 2,2-dimethyl-4,6-dioxo-1,3-dioxan-5-ylide was present at the indicated concentration.
[b]Restreaking was not continued.

Using similar procedures, the ability of the compounds of Formula I to serve as preservatives for cosmetic formulations (as demonstrated by the use of (2-nitrophenyl)-iodonium 2,2-dimethyl-4,6-dioxo-1,3-dioxan-5-ylide) was tested in a hand creme, a hand lotion, and a protein shampoo. The ingredients of the hand creme, hand lotion, and protein shampoo are listed in Tables 7, 8 and 9, respectively. In the cosmetic preservative procedures, the stock solution of (2-nitrophenyl)-iodonium 2,2-dimethyl-4,6-dioxo-1,3-dioxan-5-ylide) was made in dimethylformamide (DMF)/water solution. In addition to the bacteria listed in Table I, the following bacteria were also included in the inocula: *Klebsiella oxytoca*, *Enterobacter gergoviae*, *Pseudomonas putida* #1, and *Pseudomonas putida* #2.

The results of the cosmetic preservative tests are set forth in Tables 7, 8, 9, 10, 11, and 12.

TABLE 7

| HAND CREME FORMULATION | |
|---|---|
| Ingredient | Percent |
| Deionized Water | 67.45 |
| Carbopol 934 | 0.15 |
| Propylene Glycol | 5.00 |
| Deionized Water | 2.00 |
| Triethanolamine | 0.40 |
| Cetyl Alcohol | 1.00 |
| Stearic Acid | 2.00 |
| Mineral Oil | 15.00 |
| Arlacel 165 | 5.00 |
| Tween 80 | 0.50 |
| Isopropyl Myristate | 1.00 |
| Silicone | 0.50 |

TABLE 8

HAND LOTION FORMULATION

| Ingredient | Percent |
|---|---|
| Deionized Water | 78.60 |
| Carbopol 934 | 0.15 |
| Propylene Glycol | 5.00 |
| Stearic Acid | 3.00 |
| Stearyl Alcohol | 1.00 |
| Cetyl Alcohol | 0.50 |
| Glyceryl Monostearate SE | 4.00 |
| Mineral Oil | 5.00 |
| Silicone | 0.50 |
| Deionized Water | 2.00 |
| Triethanolamine | 0.25 |

TABLE 9

PROTEIN SHAMPOO FORMULATION[a]

| Ingredient | Percent |
|---|---|
| Deionized Water | 56.5 |
| Sodium Lauryl Ether Sulfate | 30.0 |
| Hydrolyzed Keratin Protein | 1.0 |
| Hydrolyzed Animal Protein | 4.0 |
| Cocamide DEA | 2.0 |
| Cocamidopropyl Betaine | 1.0 |
| Sodium Chloride | 0.5 |
| Citric Acid[c] | qs |

[a]All ingredients. except citric acid, were mixed at room temperature.
[b]This column totals 95 percent. The remaining 5 percent of the formulation is added either as preservative dissolved in a DMF/water solution or, in the case of the controls. water or DMF.
[c]The citric acid was used to adjust the pH between 5.5 and 6.0.

TABLE 10

HAND CREME PRESERVATION TEST[a]

| Conc. (ppm) | Streak Number | | | | | | | | | |
|---|---|---|---|---|---|---|---|---|---|---|
| | 1 | 2 | 3 | 4 | 5 | 6 | 7 | 8 | 9 | 10 |
| 100 | 1 | 1 | 1 | 1 | 1 | 1 | 1 | 1 | 4 | 7 |
| 50 | 1 | 1 | 1 | 1 | 1 | 1 | 1 | 1 | 1 | 7 |
| 10 | 1 | 1 | 1 | 1 | 1 | 5 | 1 | 8 | 1 | 7 |
| 0 (water control) | 9 | 9 | 9 | 9 | 9 | 9 | 9 | 9 | 10 | 10 |
| 0 (DMF control) | 9 | 9 | 9 | 9 | 9 | 9 | 9 | 9 | 10 | 10 |

[a]The values shown represent the growth rating obtained (see Table 4) for each particular challenge when (2-nitrophenyl)-iodonium 2,2-dimethyl-4,6-dioxo-1,3-dioxan-5-ylide was present at the indicated concentration.

TABLE 11

HAND LOTION PRESERVATION TEST[a]

| Conc. (ppm) | Streak Number | | | | | | | | | |
|---|---|---|---|---|---|---|---|---|---|---|
| | 1 | 2 | 3 | 4 | 5 | 6 | 7 | 8 | 9 | 10 |
| 100 | 1 | 1 | 1 | 1 | 1 | 1 | 1 | 1 | 1 | 1 |
| 50 | 1 | 1 | 1 | 1 | 1 | 1 | 1 | 1 | 1 | 1 |
| 25 | 1 | 1 | 1 | 1 | 1 | 1 | 1 | 1 | 1 | 2 |
| 10 | 1 | 1 | 2 | 4 | 3[b] | 9 | 7 | 9 | 10 | 10 |
| 0 (water control) | 9 | 9 | 9 | 9 | 9 | 9 | 9 | 9 | 10 | 10 |
| 0 (DMF control) | 9 | 9 | 9 | 9 | 9 | 9 | 9 | 9 | 10 | 10 |

[a]The values shown represent the growth rating obtained (see Table 4) for each particular challenge when (2-nitrophenyl)-iodonium 2,2-dimethyl-4,6-dioxo-1,3-dioxan-5-ylide was present at the indicated concentration.
[b]All colonies were fungi.

TABLE 12

PROTEIN SHAMPOO PRESERVATION TEST[a]

| Conc. (ppm) | Streak Number | | | | | | | | | |
|---|---|---|---|---|---|---|---|---|---|---|
| | 1 | 2 | 3 | 4 | 5 | 6 | 7 | 8 | 9 | 10 |
| 100 | 1 | 1 | 1 | 1 | 1 | 1 | 1 | 1 | 1 | 4 |
| 50 | 1 | 1 | 1 | 1 | 1 | 1 | 1 | 1 | 1 | 1 |
| 25 | 1 | 1 | 1 | 1 | 1 | 1 | 1 | 1 | 1 | 1 |
| 10 | 1 | 1 | 3 | 7 | 1 | 1 | 1 | 1 | 1 | 1 |
| 0 (water control) | 8 | 9 | 7 | 8 | 10 | 9 | 9 | 10 | 10 | 10 |
| 0 (DMF control) | 9 | 8 | 2 | 9 | 9 | 9 | 10 | 10 | 10 | 10 |

[a]The values shown represent the growth rating obtained (see Table 4) for each particular challenge when (2-nitrophenyl)-iodonium 2,2-dimethyl-4,6-dioxo-1,3-dioxan-5-ylide was present at the indicated concentration.

The ability of the compounds of Formula I to serve as algaecides as demonstrated by the use of (2-nitrophenyl)-iodonium 2,2-dimethyl-4,6-dioxo-1,3-dioxan-5-ylide was evaluated in a test which measures the inhibition of growth of *Selenastrum capricornutum*. Using a Coulter Counter, the growth of this algea was measured after 96 hr incubation with various levels of biocide, i.e., (2-nitrophenyl)-iodonium 2,2-dimethyl-4,6-dioxo-1,3-dioxan-5-ylide. The results of the testing are shown in Table 13.

TABLE 13

ALGAECIDE TEST[a]

| Concentration (ppm) | Percent of Control |
|---|---|
| 32 | 0.53 |
| 10 | 0.59 |
| 1.0 | 0.65 |
| 0.1 | 2.4 |
| 0.01 | 77.0 |

[a]The numbers in the "Percent of Control" column represent the percent obtained by comparing the growth of the algae in the presence of the indicated concentration of (2-nitrophenyl)-iodonium 2,2-dimethyl-4,6-dioxo-1,3-dioxan-5-ylide to the growth of the algae in the control (i.e., the growth of the algae in the absence of (2-nitrophenyl)-iodonium 2,2-dimethyl-4,6-dioxo-1,3-dioxan-5-ylide).

The compounds of Formula I are useful because of their antimicrobial activity (i.e., their ability to inhibit microorganisms) and can be used as antibacterial agents, antifungal agents, algaecidal agents or any combination thereof. Their effectiveness varies with the concentration of compound employed and the organism to be inhibited. While not all compounds are effective at similar concentrations against the same organisms, all compounds of the present invention are useful in the antimicrobial method disclosed herein.

Examples of the bacteria, fungi and algae controlled by effective amounts of one or more of the compounds of Formula I are organisms such as Bacillus species such as *Bacillus subtilis*; Pseudomonas species such as *Pseudomonas aeruginosa, Pseudomonas putida, Pseudomonas fluorescens, Pseudomonas stutzeri,* and *Pseudomonas cepacia*; Enterobacter species such as *Enterobacter aerogenes* and *Enterobacter gergoviae*; Klebsiella species such as *Klebsiella oxytoca; Escherichia coli*; Proteus species such as *Proteus vulgaris*; Staphylococcus species such as *Staphylococcus aureus*; Desulfovibrio species such as *Desulfovibrio desulfuricans*; Actinomyces species such as *Actinomyces viscosusl*; Clostridium species such as *Clostridium perfringens* and *Clostridium septicum*; Bacteroides species such as *Bacteroides fragilis* and *Bacteroides multiacidus*; Streptococcus species such as *Streptococcus faecalis, Streptococcus mutans,* and *Streptococcus bovis*;

Lactobacillus species such as *Lactobacillus casei*; Fusobacterium species such as *Fusobacterium necrophorum*; Mucor species such as *Mucor michei*; Erwinia species such as *Erwinia amylovora*; Salmonella species such as *Salmonella typhimurium*; Sphaerotilus species; Beggiatoa species; Crenothrix species; Aeromonas species; Leptothrix species; Zoogloea species; Alcoligenes species; Thiobacillus species; Candida species such as Candida albicans; Aspergillus species such as Aspergillus niger; Penicillium species; Saccharomyces species; Trichoderma species; Aureobasidium species; Selenastrum species such as Selenastrum capricornutum; Chlorella species; Volothrix species; Anacystis species; Anabaeua species; Oscillatoria species; Diatoma species; and Flagilaria species.

In the protection and preservation of inks, cosmetic formulations, adhesives, soaps, plaster, wallboard, cutting oils, textiles, polymeric materials and paper, good results are obtained when the compounds are incorporated in such products in the amount of at least 0.0001 percent by weight. In the preservation of wood, excellent results are obtained when the compounds are incorporated, by conventional treatment of the wood, in the amount of at least 0.01 pound per cubic foot (0.16 kg/cubic meter) of wood.

In the preservation and protection of oil and latex paints and primers against destruction caused by the growth of bacteria or fungi, the compounds of the present invention are preferably employed at concentrations of at least 0.0001 percent by weight.

In such operations, an effective amount of the unmodified compounds are distributed or incorporated in adhesives, soaps, inks, cosmetic formulations, wallboard, cutting oils, textiles, paper, polymeric materials, paint, lumber, wood products or growth media. However, the present method also embraces the employment of liquid or dust compositions containing the compounds. In such usage, the compounds are modified with one or a plurality of inert or antimicrobial composition adjuvants including water, organic solvents, petroleum oils, petroleum distillates, or other liquid carriers, polymeric thickening agents, urea, surface active dispersing agents and finely divided inert solids. Depending upon the concentration of the compounds used in the compositions, such augmented compositions are adapted to be distributed in inks, adhesives, soaps, cutting oils, polymeric materials, paints, textiles, wallboard, paper, lumber or soil or upon the above-ground surfaces of plants, or to be employed as concentrates and subsequently diluted with additional liquid or solid carriers to produce the ultimate treating compositions. In compositions wherein the adjuvant is a finely divided solid, a surface active agent or the combination of a surface active agent and a liquid diluent, the carrier cooperates with the active component so as to facilitate the invention and to obtain an improved result.

The exact concentration of one or more of the compounds of Formula I or Formula II to be employed in the treating compositions is not critical and may vary considerably provided the required dosage of the effective agent is supplied in the ink, cosmetic formulation, adhesive, soap, cutting oil, polymeric material, paint, textile, paper, wood or growth medium. The concentration of said compounds in liquid compositions generally is from about 0.0001 to about 3 percent by weight. Concentrations up to about 10 percent by weight may be employed. In dusts, the concentrations of the compounds can be from about 0.0001 to about 95 percent by weight. In compositions to be employed as concentrates, the compounds of Formula I can be present in a concentration of from about 0.01 to about 98 percent by weight. The quantity of treating composition to be applied to textiles, lumber, growth media and the like may vary considerably provided that the required dosage of active ingredients is applied in sufficient amounts of the finished composition to adequately facilitate the penetration and distribution of said ingredients in and on, for example, textiles, lumber and growth media and the like.

In the treatment of lumber, from about 1 to about 100 gallons of solvent composition containing one or more of the compounds of Formula I or Formula II is usually applied per 1,000 square feet (1 to 100 liters/24.543 square meters) of surface to be treated. In the pressure or vacuum treatment of lumber, sufficient composition is employed adequately to impregnate the wood.

In the preparation of dust compositions, one or more of the compounds of Formula I can be admixed with any of the finely divided solids, such as pyrophyllite, talc, chalk and gypsum and the like. In such operations, the finely divided carrier is ground or mixed with the said compounds or wet with a solution of the compounds in a volatile organic solvent. Similarly, dust compositions containing the products can be prepared using various solid surface active dispersing agents such as fuller's earth, bentonite, attapulgite and other clays. Depending upon the proportions of ingredients, these dust compositions can be employed for the control of pests or employed as concentrates and subsequently diluted with an additional solid surface active dispersing agent or with pyrophyllite, chalk, talc, gypsum and the like to obtain the desired amount of active ingredient in a composition adapted to be employed as described herein. Also, such dust compositions when employed as concentrates can be dispersed in water, with or without the aid of dispersing agents to form spray mixtures.

Further, spray compositions can be prepared by incorporating one or more of the compounds of Formula I, or their liquid or dust concentrate compositions, in mixtures with surface active dispersing agents such as an ionic or non-ionic emulsifying agent. Such spray compositions are readily employed for the control of microbes or are dispersed in liquid carriers to form diluted sprays containing the compounds in any desired amount suitable for microbial control. The choice of dispersing agents and amounts thereof employed are determined by the ability of the agents to facilitate the dispersion of the concentrate in the liquid carrier to produce the desired spray compositions.

Similarly, the compounds of Formula I can be admixed with a suitable water-immiscible organic liquid and a surface active dispersing agent to produce an emulsifiable concentrate which can be further diluted with water and oil to form spray mixtures in the form of oil-in-water emulsions. In such compositions, the carrier comprises an aqueous emulsion, i.e., a mixture of water-immiscible solvent, emulsifying agent and water. Preferred dispersing agents which can be employed in these compositions are oil-soluble and include the nonionic emulsifiers such as the condensation products of alkylene oxides with the inorganic acids, polyoxyethylene derivatives or sorbitan esters, complex ether alcohols and the like. Suitable organic liquids which can be employed in the composition include petroleum oils and distillates, toluene, liquid halohydrocarbons and synthetic organic oils. The surface active dispersing agents are usually employed in liquid compositions in the amount of from about 0.1 to about 10 to about 20 percent by weight of the combined weight of the dispersing agent and active compound.

In addition, other liquid compositions containing the desired amount of one or more of the compounds of Formula I or Formula II can be prepared by dissolving said compounds in an organic liquid such as acetone, methylene chloride, chlorobenzene and petroleum distillates. The preferred organic solvent carriers are those which are adapted to accomplish the penetration and impregnation of the environment to be treated.

In further embodiments, the compounds as employed in accordance with the present invention, or compositions containing the same, can be advantageously employed in the methods described herein in combination with one or more pesticidal or preservative compounds. In such embodiment, such pesticidal or preservative compound is employed either as a supplemental active constituent, an additament or as an adjuvant. Representative pesticidal or preservative compounds include the substituted phenols, cresols, substituted cresols and their metal salts, the bisphenols and thiobisphenols, the halogenated salicylanilides, the organosulfur compounds, the carbamate compounds, the quaternary ammonium compounds, the organometallic compounds, the inorganic salts and miscellaneous other compounds.

What is claimed is:

1. A compound of the formula

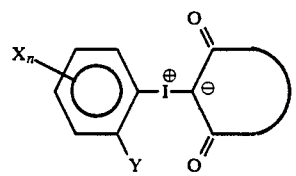

wherein
each X independently represents halo, alkyl of 1 to 4 carbon atoms inclusive, or alkoxy of 1 to 4 carbon atoms inclusive;
n represents an integer from 0 to 2;
Y represents a nitro, alkyl sulfinyl, alkyl sulfonyl, carboxylic acid and the esters and amides thereof, or a sulfonic acid and the amides thereof, group; and

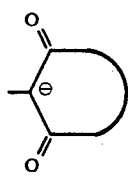

represents a cyclic 1,3-dione anion consisting of a monocyclic or bicyclic, saturated or unsaturated ring system comprised of five- and/or six-membered rings optionally containing oxygen or nitrogen atoms and optionally substituted with from 1 to 2 substituents selected from the group consisting of halo, alkyl of 1 to 4 carbon atoms inclusive, alkoxy of 1 to 4 carbon atoms inclusive, and carboxyl; and their hydrates and alcoholates,
with the proviso that those compounds wherein both Y represents nitro and

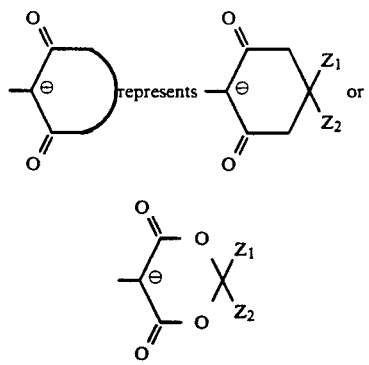

wherein $Z_1$ and $Z_2$ independently represent hydrogen or an alkyl group, are excluded.

2. The compound of claim 1 in which Y represents nitro, alkyl sulfinyl or alkyl sulfonyl.

3. The compound of claim 2 in which the cyclic 1,3-dione anion is selected from the group consisting of

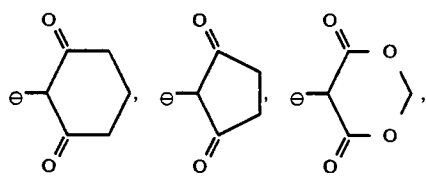

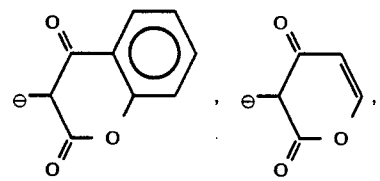

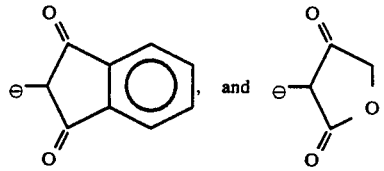

each of which may be optionally substituted with from 1 to 2 substituents selected from the group consisting of halo, alkyl of 1 to 4 carbon atoms inclusive, alkoxy of 1 to 4 carbon atoms inclusive and carboxyl.

4. A method of inhibiting the growth of microorganisms which comprises contacting said microorganisms or habitat thereof, with an effective amount of a compound of the formula

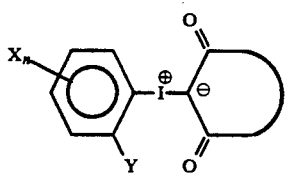

wherein
each X independently represents halo, alkyl of 1 to 4 carbon atoms inclusive, or alkoxy of 1 to 4 carbon atoms inclusive;
n represents an integer from 0 to 2;

Y represents a nitro, alkyl sulfinyl, alkyl sulfonyl, carboxylic acid and the esters and amides thereof, or a sulfonic acid and the amides thereof, group; and

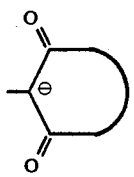

represents a cyclic 1,3-dione anion consisting of a monocyclic or bicyclic, saturated or unsaturated ring system comprised of five- and/or six-membered rings optionally containing oxygen or nitrogen atoms and optionally substituted with from 1 to 2 substituents selected from the group consisting of halo, alkyl of 1 to 4 carbon atoms inclusive, alkoxy of 1 to 4 carbon atoms inclusive, and carboxyl; and their hydrates and alcoholates.

5. The method of claim 4 in which Y represents nitro, alkyl sulfinyl or alkyl sulfonyl.

6. The method of claim 5 in which the cyclic 1,3-dione anion is selected from the group consisting of

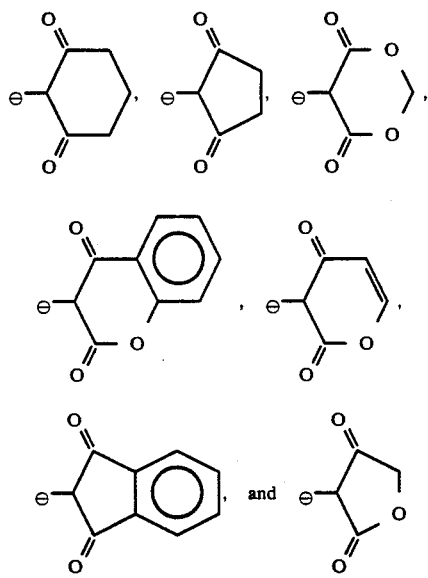

each of which may be optionally substituted with from 1 to 2 substituents selected from the group consisting of halo, alkyl of 1 to 4 carbon atoms inclusive, alkoxy of 1 to 4 carbon atoms inclusive and carboxyl.

7. An antimicrobial composition comprising inert or antimicrobial composition adjuvants in combination with an effective amount of a compound of the formula

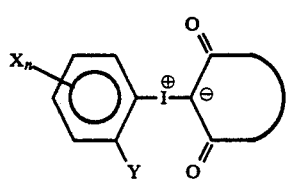

wherein each X independently represents halo, alkyl of 1 to 4 carbon atoms inclusive, or alkoxy of 1 to 4 carbon atoms inclusive;

n represents an integer from 0 to 2;

Y represents a nitro, alkyl sulfinyl, alkyl sulfonyl, carboxylic acid and the esters and amides thereof, or a sulfonic acid and the amides thereof, group; and

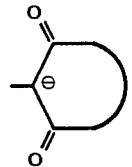

represents a cyclic 1,3-dione anion consisting of a monocyclic or bicyclic, saturated or unsaturated ring system comprised of five- and/or six-membered rings optionally containing oxygen or nitrogen atoms and optionally substituted with from 1 to 2 substituents selected from the group consisting of halo, alkyl of 1 to 4 carbon atoms inclusive, alkoxy of 1 to 4 carbon atoms inclusive, and carboxyl; and their hydrates and alcoholates, with the proviso that those compounds where both Y represents nitro and

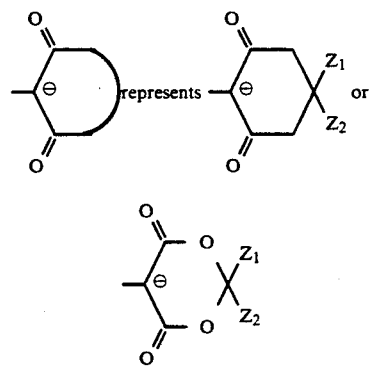

wherein $Z_1$ and $Z_2$ independently represent hydrogen or an alkyl group, are excluded.

8. The composition of claim 7 in which Y represents nitro, alkyl sulfinyl or alkyl sulfonyl.

9. The composition of claim 8 in which the cyclic 1,3-dione anion is selected from the group consisting of

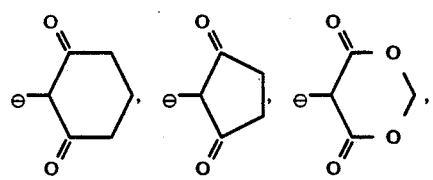

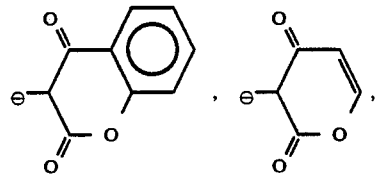

-continued
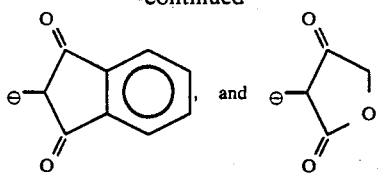
each of which may be optionally substituted with from 1 to 2 substituents selected from the group consisting of halo, alkyl of 1 to 4 carbon atoms inclusive, alkoxy of 1 to 4 carbon atoms inclusive and carboxyl.
* * * * *